(12) United States Patent
Iwashita et al.

(10) Patent No.: US 12,146,135 B2
(45) Date of Patent: Nov. 19, 2024

(54) METHOD FOR EDITING FILAMENTOUS FUNGAL GENOME THROUGH DIRECT INTRODUCTION OF GENOME-EDITING PROTEIN

(71) Applicants: NATIONAL RESEARCH INSTITUTE OF BREWING, Higashihiroshima (JP); FASMAC CO., LTD., Atsugi (JP)

(72) Inventors: Kazuhiro Iwashita, Higashihiroshima (JP); Ken Oda, Higashihiroshima (JP); Kohei Shimamoto, Higashihiroshima (JP); Yusaku Wada, Atsugi (JP)

(73) Assignees: NATIONAL RESEARCH INSTITUTE OF BREWING, Higashihiroshima (JP); FASMAC CO., LTD., Atsugi (JP)

( * ) Notice: Subject to any disclaimer, the term of this patent is extended or adjusted under 35 U.S.C. 154(b) by 1248 days.

(21) Appl. No.: 16/473,492

(22) PCT Filed: Aug. 25, 2017

(86) PCT No.: PCT/JP2017/030501
§ 371 (c)(1),
(2) Date: Oct. 4, 2019

(87) PCT Pub. No.: WO2018/123134
PCT Pub. Date: Jul. 5, 2018

(65) Prior Publication Data
US 2020/0040330 A1 Feb. 6, 2020

(30) Foreign Application Priority Data
Dec. 26, 2016 (JP) .................... 2016-250518

(51) Int. Cl.
*C12N 15/11* (2006.01)
*C12N 9/22* (2006.01)

(52) U.S. Cl.
CPC .............. *C12N 15/11* (2013.01); *C12N 9/22* (2013.01); *C12N 2310/20* (2017.05); *C12N 2800/80* (2013.01)

(58) Field of Classification Search
CPC ..... C12N 9/22; C12N 2310/20; C12N 15/905
See application file for complete search history.

(56) References Cited

FOREIGN PATENT DOCUMENTS

WO WO 2015/054507 A1 4/2015

OTHER PUBLICATIONS

Pohl et al. CRISPR/Cas9 based genome editing of Penicillium chrysogenum. ACS Synthetic Biology, vol. 5, pp. 754-764, and pp. 1/11-11/11 of Supporting Information, Apr. 12, 2016. (Year: 2016).*
Ramakrishna et al. Gene disruption by cell-penetrating peptide-mediated delivery of Cas9 protein and guide RNA. Genome Research, vol. 24, No. 6, pp. 1020-1027, 2014. (Year: 2014).*
Katayama et al. Development of a genome editing technique using the CRISPR/Cas9 system in the industrial filamentous fungus *Aspergillus oryzae*. Biotechnology Letters, vol. 38, pp. 637-642 and pp. 1/7-7/7 of Supplementary Information, 2016, published online Dec. 19, 2015. (Year: 2015).*
Du et al. Construction of brewing-wine Aspergillus oryzae pyrG-mutant by pyrG gene deletion and its application in homology transformation. Acta Biochimica Biophysica Sinica, vol. 46, No. 6, pp. 477-483, Apr. 16, 2014. (Year: 2014).*
Fuller et al. Development of the CRISPR/Cas9 system for targeted gene disruption in Aspergillus fumigatus. Eukaryotic Cell, vol. 14, No. 11, pp. 1073-1080, and pp. 1/6-6/6 of Supplemental Material, Aug. 28, 2015. (Year: 2015).*
Sfeir et al. Microhomology-Mediated End Joining: A Back-up Survival Mechanism or Dedicated Pathway? Trends in Biochemical Sciences. vol. 40, No. 11, pp. 701-714, Oct. 1, 2015. (Year: 2015).*
Qin et al. CRISPR-Cas9 assisted gene disruption in the higher fungus *Ganoderma* species. Process Biochemistry, vol. 56, pp. 57-61, 2017, online Feb. 16, 2017. (Year: 2017).*
https://horizondiscovery.com/en/ordering-and-calculation-tools/nmol-to-ug-calculator, printed as p. 1/1 on Sep. 6, 2023. ( Year: 2023).*
Clikeman et al. Homologous recombination repair of double-strand breaks in yeast is enhanced by MAT heterozygosity through yKU-dependent and- independent mechanisms. Genetics, vol. 157, pp. 579-589, Feb. 2001. (Year: 2001).*
Shaw, William. "Quick and easy CRISPR engineering in *Saccharomyces cerevisiae*." URL: https://benchling. com/pub/ellis-crispr-tools (2016). (Year: 2016).*
Krappmann, S. Gene targeting in filamentous fungi: the benefits of impaired repair. Fungal Biology Reviews, vol. 21, pp. 25-29, 2007. (Year: 2007).*
Aida et al., "Cloning-free CRISPR/Cas System Facilitates Functional Cassette Knock-in in Mice," Genome Biology, vol. 16, No. 87, 2015, 11 pages.
Fuller et al., "Development of the CRISPR/Cas9 System for Targeted Gene Disruption in Aspergillus fumigatus," Eukaryotic Cell, vol. 14, No. 11, Nov. 2015, pp. 1073-1080.

(Continued)

*Primary Examiner* — Jennifer Dunston
(74) *Attorney, Agent, or Firm* — Birch, Stewart, Kolasch & Birch, LLP

(57) ABSTRACT

The present invention relates to a method of editing a filamentous fungal genome by direct introduction of a genome editing protein molecule or complex. The method includes three modes. In the first mode, a genome editing protein molecule or complex for a target gene is directly introduced into a cell of an *Aspergillus* fungus, to edit a gene in the *Aspergillus* fungal genome. In the second mode, a genome editing protein molecule or complex for a target region in a filamentous fungal genome, and a desired DNA fragment, are directly introduced into a filamentous fungal cell, to knock-in the DNA fragment to a desired target site in the filamentous fungal genome. In the third mode, genome editing protein molecules or complexes for plural target genes are directly introduced into a filamentous fungal cell, to carry out simultaneous editing of the plural genes in the filamentous fungal genome.

13 Claims, 4 Drawing Sheets
Specification includes a Sequence Listing.

(56) References Cited

OTHER PUBLICATIONS

Gupta et al., "Gene Editing for Cell Engineering: Trends and Applications," Critical Reviews in Biotechnology, vol. 37, No. 5, 2017 (Published online Aug. 18, 2016), pp. 672-684 (14 pages total).

International Preliminary Report on Patentability and English translation of the Written Opinion of the International Searching Authority, dated Jul. 11, 2019, for International Application No. PCT/JP2017/030501.

International Search Report, dated Nov. 21, 2017, for corresponding International Application No. PCT/JP2017/030501, with an English translation.

Katayama et al., "Development of a Genome Editing Technique Using the CRISPR/Cas9 System in the Industrial Filamentous Fungus Aspergillus oryzae," Biotechnol Lett, vol. 38, 2016 (Published online Dec. 19, 2015), pp. 637-642.

Kim et al., "Highly Efficient RNA-guided Genome Editing in Human Cells via Delivery of Purified Cas9 Ribonucleoproteins," Genome Research, vol. 24, 2014, pp. 1012-1019 (16 pages total).

Kotani et al., "Efficient Multiple Genome Modifications Induced by the crRNAs, tracrRNA and Cas9 Protein Complex in Zebrafish," PLoS One, May 26, 2015, pp. 1-16 (23 pages total).

Nødvig et al, "A CRISPR-Cas9 System for Genetic Engineering of Filamentous Fungi," PLoS One, vol. 10, Jul. 15, 2015, pp. 1-18.

Pohl et al., "CRISPR/Cas9 Based Genome Editing of Penicillium chrysogenum," ACS Synthetic Biology, vol. 5, 2016 (Published Apr. 12, 2016), pp. 754-764 (22 pages total).

Sander et al., "CRISPR-Cas Systems for Editing, Regulating and Targeting Genomes," Nature Biotechnology, vol. 32, No. 4, Apr. 2014 (Published online Mar. 2, 2014), pp. 347-355.

Stella et al., "The Genome Editing Revolution: A CRISPR-Cas TALE Off-target Story," Bioessays, vol. 38, 2016, pp. S4-S13.

Yamamoto et al., "Genome Editing with Programmable Site-specific Nucleases," UIRUSA, vol. 64, No. 1, 2014, pp. 75-82, with English abstract.

Zhang et al., "Highly Efficient CRISPR Mutagenesis by Microhomology-Mediated end Joining in Aspergillus fumigatus," Fungi Genetics and Biology, vol. 86, 2016 (Available online Dec. 14, 2015), pp. 47-57.

* cited by examiner

* Fwd: PCR using primers wANest-F and 1bpCheck
* Rev: PCR using primers 1bpCheck and wANest-R

SEQUENCE LISTING

<160> NUMBER OF SEQ ID NOS: 26

<210> SEQ ID NO 1
<211> LENGTH: 21
<212> TYPE: DNA
<213> ORGANISM: Aspergillus oryzae

<400> SEQUENCE: 1
gacttcccct acggctccga g                                        21

<210> SEQ ID NO 2
<211> LENGTH: 80
<212> TYPE: RNA
<213> ORGANISM: Artificial Sequence
<220> FEATURE:
<223> OTHER INFORMATION: chimeric sequence of crRNA and tracrRNA

<400> SEQUENCE: 2
guuuuagagc uagaaauagc aaguuaaaau aaggcuaguc cguuaucaac uugaaaagu    60 ggcaccgagu cggugcuuuu                                              80

<210> SEQ ID NO 3
<211> LENGTH: 101
<212> TYPE: RNA
<213> ORGANISM: Artificial Sequence
<220> FEATURE:
<223> OTHER INFORMATION: single guide RNA for targeting pyrG gene

<400> SEQUENCE: 3
gacuuccccu acggcuccga gguuuuagag cuagaaauag caaguuaaaa uaaggcuagu    60
ccguuaucaa cuugaaaaag uggcaccgag ucggugcuuu u                      101

<210> SEQ ID NO 4

-continued

```
<211> LENGTH: 22
<212> TYPE: DNA
<213> ORGANISM: Artificial Sequence
<220> FEATURE:
<223> OTHER INFORMATION: primer pyrGfullA

<400> SEQUENCE: 4
gggagacaaa gctaacaacg tc                                             22

<210> SEQ ID NO 5
<211> LENGTH: 21
<212> TYPE: DNA
<213> ORGANISM: Artificial Sequence
<220> FEATURE:
<223> OTHER INFORMATION: primer pyrGfullB

<400> SEQUENCE: 5
gtatgcacag tcaggactcc a                                              21

<210> SEQ ID NO 6
<211> LENGTH: 20
<212> TYPE: DNA
<213> ORGANISM: Artificial Sequence
<220> FEATURE:
<223> OTHER INFORMATION: primer pyrGseqA

<400> SEQUENCE: 6
gcccttgcag agaagcacaa                                                20

<210> SEQ ID NO 7
<211> LENGTH: 20
<212> TYPE: DNA
<213> ORGANISM: Artificial Sequence
<220> FEATURE:
<223> OTHER INFORMATION: primer pyrGseqB

<400> SEQUENCE: 7
aggtgacgtg tcgagacgaa                                                20

<210> SEQ ID NO 8
<211> LENGTH: 24
<212> TYPE: DNA
<213> ORGANISM: Artificial Sequence
<220> FEATURE:
<223> OTHER INFORMATION: primer pyrGpcrA

<400> SEQUENCE: 8
ctgctggatt tggctgaccg tatg                                           24

<210> SEQ ID NO 9
<211> LENGTH: 24
<212> TYPE: DNA
<213> ORGANISM: Artificial Sequence
<220> FEATURE:
<223> OTHER INFORMATION: primer pyrGpcrB

<400> SEQUENCE: 9
gtttggtact gctgtcccag cttg                                           24

<210> SEQ ID NO 10
<211> LENGTH: 21
<212> TYPE: DNA
<213> ORGANISM: Aspergillus oryzae

<400> SEQUENCE: 10
gaaagatgcc tcgcagctta t                                              21
```

```
<210> SEQ ID NO 11
<211> LENGTH: 101
<212> TYPE: RNA
<213> ORGANISM: Artificial Sequence
<220> FEATURE:
<223> OTHER INFORMATION: single guide RNA for targeting wA gene

<400> SEQUENCE: 11
gaaagaugcc ucgcagcuua uguuuuagag cuagaaauag caaguuaaaa uaaggcuagu      60
ccguuaucaa cuugaaaaag uggcaccgag ucggugcuuu u                        101

<210> SEQ ID NO 12
<211> LENGTH: 25
<212> TYPE: DNA
<213> ORGANISM: Artificial Sequence
<220> FEATURE:
<223> OTHER INFORMATION: primer wAseqF

<400> SEQUENCE: 12
cctaatccgg ctctggagag tgcgt                                           25

<210> SEQ ID NO 13
<211> LENGTH: 29
<212> TYPE: DNA
<213> ORGANISM: Artificial Sequence
<220> FEATURE:
<223> OTHER INFORMATION: primer wAseqR

<400> SEQUENCE: 13
atcctgtcga catctcggcc atagtacag                                       29

<210> SEQ ID NO 14
<211> LENGTH: 33
<212> TYPE: DNA
<213> ORGANISM: Artificial Sequence
<220> FEATURE:
<223> OTHER INFORMATION: primer 1bpCheck

<400> SEQUENCE: 14
tcatctccgc aaggatcaaa aggcccctct cgg                                  33

<210> SEQ ID NO 15
<211> LENGTH: 35
<212> TYPE: DNA
<213> ORGANISM: Artificial Sequence
<220> FEATURE:
<223> OTHER INFORMATION: primer wAleftA-F

<400> SEQUENCE: 15
gatggccctc tattttgtgc aaagactgac atgac                                35

<210> SEQ ID NO 16
<211> LENGTH: 32
<212> TYPE: DNA
<213> ORGANISM: Artificial Sequence
<220> FEATURE:
<223> OTHER INFORMATION: primer wArightD-R

<400> SEQUENCE: 16
ggtaggaagc cttgacagcc agcatggcgt gt                                   32

<210> SEQ ID NO 17
<211> LENGTH: 51
<212> TYPE: DNA
```

<213> ORGANISM: Artificial Sequence
<220> FEATURE:
<223> OTHER INFORMATION: Synthetic: reference

<400> SEQUENCE: 17
cggccgagga cttcccctac ggctccgaga ggggccttttt gatccttgcg g        51

<210> SEQ ID NO 18
<211> LENGTH: 50
<212> TYPE: DNA
<213> ORGANISM: Artificial Sequence
<220> FEATURE:
<223> OTHER INFORMATION: Synthetic: GeKS1-2, 6, ..., 35

<400> SEQUENCE: 18
cggccgagga cttcccctac ggctcgagag gggccttttg atccttgcgg           50

<210> SEQ ID NO 19
<211> LENGTH: 41
<212> TYPE: DNA
<213> ORGANISM: Artificial Sequence
<220> FEATURE:
<223> OTHER INFORMATION: Synthetic: GeKS1-17

<400> SEQUENCE: 19
cggccgagga cttcccgaga ggggccttttt gatccttgcg g                   41

<210> SEQ ID NO 20
<211> LENGTH: 35
<212> TYPE: DNA
<213> ORGANISM: Artificial Sequence
<220> FEATURE:
<223> OTHER INFORMATION: Synthetic: GeKS1-8

<400> SEQUENCE: 20
cggccgagga cttcccctac gtttgatcct tgcgg                           35

<210> SEQ ID NO 21
<211> LENGTH: 39
<212> TYPE: DNA
<213> ORGANISM: Artificial Sequence
<220> FEATURE:
<223> OTHER INFORMATION: Synthetic: GeKS1-14

<400> SEQUENCE: 21
cggccgagga cttcccctac ggcttttttga tccttgcgg                      39

<210> SEQ ID NO 22
<211> LENGTH: 25
<212> TYPE: DNA
<213> ORGANISM: Artificial Sequence
<220> FEATURE:
<223> OTHER INFORMATION: Synthetic: GeKS1-21

<400> SEQUENCE: 22
cggccgagga cttcccctat tgcgg                                      25

<210> SEQ ID NO 23
<211> LENGTH: 23
<212> TYPE: DNA
<213> ORGANISM: Artificial Sequence
<220> FEATURE:
<223> OTHER INFORMATION: Synthetic: GeKS1-3

<400> SEQUENCE: 23 gagggggcctt ttgatccttg cgg                                       23

```
<210> SEQ ID NO 24
<211> LENGTH: 19
<212> TYPE: DNA
<213> ORGANISM: Artificial Sequence
<220> FEATURE:
<223> OTHER INFORMATION: Synthetic: GeKS1-12

<400> SEQUENCE: 24
cggccgagga cttcccta                                              19

<210> SEQ ID NO 25
<211> LENGTH: 25
<212> TYPE: DNA
<213> ORGANISM: Artificial Sequence
<220> FEATURE:
<223> OTHER INFORMATION: Synthetic: GeKS1-15

<400> SEQUENCE: 25 gagagggggcc ttttgatcct tgcgg                                     25

<210> SEQ ID NO 26
<211> LENGTH: 25
<212> TYPE: DNA
<213> ORGANISM: Artificial Sequence
<220> FEATURE:
<223> OTHER INFORMATION: Synthetic: GeKS1-27, 29, 33

<400> SEQUENCE: 26
cggccgagga cttcccctac ggctc                                      25
```

METHOD FOR EDITING FILAMENTOUS FUNGAL GENOME THROUGH DIRECT INTRODUCTION OF GENOME-EDITING PROTEIN

REFERENCE TO ELECTRONIC SEQUENCE LISTING

The application contains a Sequence Listing which has been submitted electronically in .txt format and is hereby incorporated by reference in its entirety. Said .txt copy, created on Jun. 16, 2023, is named "2023 Jun. 16 0760-0511PUS1_ST25.txt" and is 5,556 bytes in size. The sequence listing contained in this .txt file is part of the specification and is hereby incorporated by reference herein in its entirety.

TECHNICAL FIELD

The present invention relates to a method of editing a filamentous fungal genome by direct introduction of a genome editing protein molecule or complex.

BACKGROUND ART

Genome editing is a technique for introducing a mutation such as a base deletion, or inserting another gene, into a particular site in a genome using the Cas9 gene or the like (Non-Patent Documents 1 to 3). Studies using TALEN, Cas9, Cpf1, or PPR have been carried out for a variety of biological species including human and plants. Conventional techniques can be roughly divided into methods in which a gene encoding TALEN or Cas9 is introduced into an organism, and methods in which these proteins are directly introduced.

For organisms (human cells, plant cells) other than the genus *Aspergillus*, there have been a number of study reports on genome editing by direct introduction of a Cas9 protein or the like in organisms (human cells, plant cells) except the genus *Aspergillus* (for example, Non-Patent Documents 4 to 6). In filamentous fungi, a direct introduction method has been reported for the genus *Penicillium* (Non-Patent Document 7), but there has been no report for the genus *Aspergillus*. Papers on gene knock-in, knock-out, or multi-genome editing (editing of two or more sites at once) that have been reported so far include those for human or frog eggs, and plants. However, there has been no report for filamentous fungi including the genus *Aspergillus*.

PRIOR ART DOCUMENT(S)

Non-Patent Document(s)

Non-Patent Document 1: Yamamoto T. et al. (2014). Genome editing with programmable site-specific nucleases. Uirusu. 64 (1): 75-82.
Non-Patent Document 2: Gupta S K. et al. (2016 August). Gene editing for cell engineering: trends and applications. Crit Rev Biotechnol. Pages 1-13.
Non-Patent Document 3: Stella S. et al. (2016 July) The genome editing revolution: A CRISPR-Cas TALE off-target story. Bioessays. 38 Suppl 1: S4-S13.
Non-Patent Document 4: Kotani H. et al. (2015 May). Efficient multiple genome modifications induced by the crRNAs, tracrRNA and Cas9 Protein complex in zebrafish. Plos ONE. 26; 10 (5): e0128319.
Non-Patent Document 5: Aida T. et al. (2015 April). Cloning-free CRISPR/Cas system facilitates functional cassette knock-in in mice. Genome Biol. 16:87.
Non-Patent Document 6: Kim S. et al. (2014 June). Highly efficient RNA-guided genome editing in human cells via delivery of purified Cas9 ribonucleoproteins. Genome Res. 24 (6): 1012-9.
Non-Patent Document 7: Pohl et al., ACS Synthetic Biology, 2016 Jul. 15; 5 (7): 754-764.

SUMMARY OF THE INVENTION

Problems to be Solved by the Invention

An object of the present invention is to develop and provide a genome editing technique practically applicable to a variety of filamentous fungi such as *Aspergillus* fungi, including koji fungi.

Means for Solving the Problems

As a result of intensive study, the present inventors established a genome editing technique in which a complex containing a Cas9 protein and a guide RNA is directly introduced into a koji fungal protoplast to introduce a deletion mutation into a desired site in a genome, and further, successfully established, also in koji fungi, a knock-in-based genome editing technique and a technique that enables simultaneous editing of a plurality of target genes, thereby completing the present invention.

More specifically, the present invention provides a method of editing a gene in an *Aspergillus* fungal genome, the method comprising the step of: directly introducing a genome editing protein molecule or complex for a target gene into a cell of an *Aspergillus* fungus; and a method of producing an *Aspergillus* fungal strain in which a gene in a genome is edited, the method comprising the steps of: directly introducing a genome editing protein molecule or complex for a target gene into cells of an *Aspergillus* fungus; and selecting and collecting an *Aspergillus* fungal cell in which the target gene is edited (first mode).

The present invention also provides a method of editing a filamentous fungal genome by knock-in, the method comprising the step of: directly introducing a genome editing protein molecule or complex for a target region in a filamentous fungal genome, and a desired DNA fragment, into a filamentous fungal cell: wherein the genome editing protein molecule or complex has a DNA cleavage activity; and a method of producing a filamentous fungal strain having a genome edited by knock-in, the method comprising the steps of: directly introducing a genome editing protein molecule or complex for a target region in a filamentous fungal genome, said molecule or complex having a DNA cleavage activity, and a desired DNA fragment, into filamentous fungal cells; and selecting and collecting a filamentous fungal cell in which the desired DNA fragment is inserted at a cleavage site in the target region (second mode).

The present invention also provides a method of editing a plurality of genes in a filamentous fungal genome, the method comprising the step of: directly introducing a first genome editing protein molecule or complex for a first target gene, and a second genome editing protein molecule or complex for a second target gene, into a filamentous fungal cell; and a method of producing a filamentous fungal strain having a plurality of edited genes in a genome, the method comprising the steps of: directly introducing a first genome editing protein molecule or complex for a first target gene, and a second genome editing protein molecule or complex for a second target gene, into filamentous fungal cells; and selecting and collecting a filamentous fungal cell in which the first and second target genes are edited (third mode).

Effect of the Invention

By the present invention, a genome editing method in which a genome editing protein molecule or complex is directly introduced into a filamentous fungus such as an *Aspergillus* fungus is provided. In a genome editing method in which a protein is directly introduced into a cell, no DNA fragment is introduced into a genome. Therefore, there has been an opinion that the resulting cell is not a gene recombinant (that is, indistinguishable from a natural mutant), and the method is thus attracting attention from industries. In particular, according to the simultaneous editing method (multiplex genome editing method) of the third mode of the present invention, screening for a first target gene for which positive selection can be carried out makes it possible to isolate a strain in which a gene for which positive selection cannot be carried out or a gene whose phenotype is not evident has been edited.

MODE FOR CARRYING OUT THE INVENTION

Figure 1:
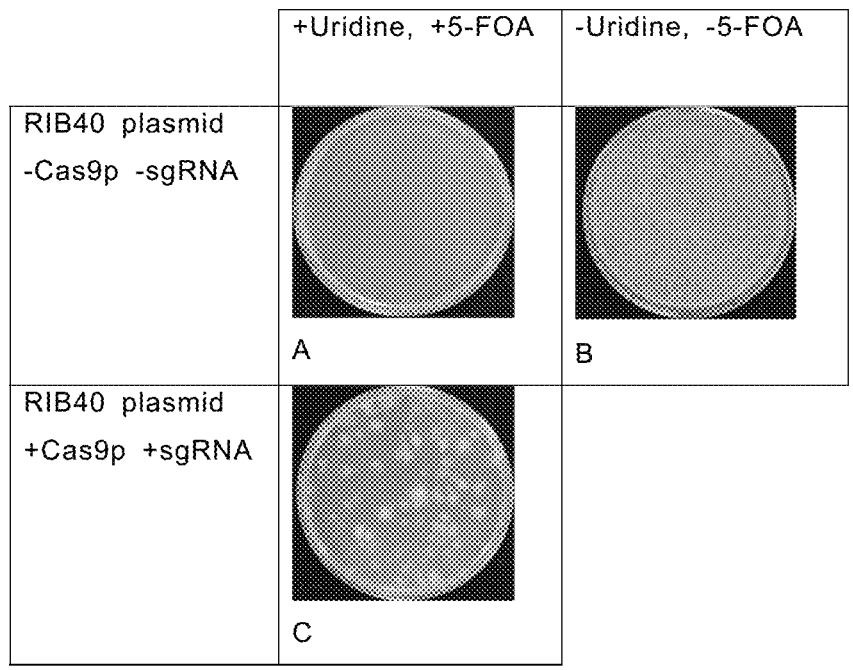
FIG. 1, panels A, B and C, shows the result of an attempt to disrupt the pyrG gene by directly introducing a Cas9 protein-guide RNA complex (ribonucleoprotein) for the pyrG gene into protoplasts of the *Aspergillus oryzae* RIB40 strain in Example 1. As shown in Panel A, colonies did not grow on a 5-FOA-containing selection medium, since the ribonucleoprotein was not introduced and thus the pyrG gene was not disrupted. On the other hand, as shown in Panel C, a strain whose pyrG gene was disrupted by direct introduction of the ribonucleoprotein grew to form colonies on the 5-FOA-containing selection medium.

The present invention is a method of editing a genome of a filamentous fungus such as an *Aspergillus* fungus, wherein a genome editing protein molecule or complex is directly introduced into a filamentous fungal cell to edit the filamentous fungal genome. The term "direct introduction" does not mean that a nucleic acid encoding a protein is introduced into a cell to express the protein from the nucleic acid in the cell, but means that a protein is incorporated into a cell.

The genome editing protein direct introduction method of the present invention includes three modes. Details of the method are described later. Briefly, the first mode is a technique in which a genome editing protein molecule or complex is introduced into a cell of an *Aspergillus* fungus, to obtain a genome-edited strain in which a target gene is modified at a desired site. The second mode is a technique in which a genome editing protein molecule or complex that cleaves DNA, and a desired DNA fragment, are directly introduced into a cell of a filamentous fungal cell, to obtain a genome-edited strain in which the desired DNA fragment is knocked into a DNA cleavage site. The third mode is a technique in which two or more sets of genome editing protein molecules or complexes are directly introduced into a filamentous fungal cell, to carry out simultaneous editing of a plurality of target genes.

Examples of the filamentous fungus include not only *Aspergillus* fungi, but also various filamentous fungi such as those belonging to the genera *Penicillium, Monascus, Eurotium, Neosartorya, Gibberella, Fusarium*, and *Magnaporthe*. The filamentous fungus is preferably, but not limited to, an *Aspergillus* fungus. Examples of the *Aspergillus* fungus include koji fungi such as kikoji fungus (*Aspergillus oryzae*), kurokoji fungus (*Aspergillus luchuensis* and the like), and shirokoji fungus (*Aspergillus usamii, Aspergillus kawachii*, and the like); and *Aspergillus* fungi other than koji fungi, such as *Aspergillus niger* and *Aspergillus flavus*. The *Aspergillus* fungus is preferably a koji fungus, more preferably kikoji fungus (*Aspergillus oryzae*).

In the present invention, the term "genome editing" or "genome modification" refers to introduction of a mutation into a desired site in a genome with high specificity. Examples of the mutation herein include substitution, deletion, translocation, inversion, and insertion of one or more bases. Examples of the base insertion include insertion of a desired gene fragment.

The "genome editing protein molecule or complex" means a protein molecule or complex having an activity to recognize a desired target sequence in a genome and to cleave a DNA strand(s) or convert one or more bases within the target sequence or its vicinity, and does not include restriction enzymes, which recognize a palindrome sequence to cleave a DNA double-strand. A protein molecule that itself has an ability to recognize the target sequence in the genome and to recruit itself into the target sequence portion may be used. Or, a complex containing a protein molecule having a DNA cleavage activity or base conversion activity and a guide nucleic acid molecule that recruits the protein molecule into the target sequence portion in the genome may be used. The term "protein molecule" includes fusion proteins.

As the guide nucleic acid molecule, a single-stranded polynucleotide, especially preferably a single-stranded RNA, may be used. When a single-stranded polynucleotide is used as the guide nucleic acid molecule, the guide nucleic acid molecule hybridizes with the complementary strand of the target sequence recognized by the genome editing protein complex, to cause recruitment of the complex into the target sequence portion.

The cleavage of the DNA strand may be in a mode in which both strands of a double-stranded DNA are cleaved at the same site, or may be in a mode in which the strands are cleaved within a narrow region (typically within a region of not more than one hundred and several ten base pairs, or not more than several ten base pairs). One genome editing protein molecule or complex may have an activity to cleave both strands of double-stranded DNA. Or, genome editing proteins or complexes each of which cleaves one strand of a double-stranded DNA may be used in combination.

The "genome editing protein molecule or complex for a target gene" means a genome editing protein molecule or complex for editing or modifying a target gene. Such a genome editing protein molecule or complex is usually designed such that the target site of the DNA cleavage or base alteration by the molecule or complex is positioned within a target gene region, typically within a coding exon region. The "gene region" means a continuous region in a genome, which region contains a protein-coding region (coding exon region), an intron region, and a region that may be involved in regulation of expression of the gene, such as a promoter region or a 5'- or 3'-UTR. For example, in cases where a target gene is to be edited using a genome editing protein molecule or complex whose target site is a particular site in a target sequence, the target sequence may be set such that at least the particular site is positioned within a coding exon region.

When the term "genome editing protein molecule or complex for a target region" is mentioned, the genomic region to be edited or modified by the molecule or complex is not limited to a gene region.

Specific examples of the genome editing protein molecule or complex include a TALEN protein; a ZFN protein: a complex containing a Cas9 protein and a guide RNA: complexes containing a nickase-modified Cas9 protein and each of a pair of guide RNAs; a complex containing a nickase-modified or null mutant Cas9 protein to which a deaminase is linked and a guide RNA: a complex containing a Cpf1 protein and a guide RNA; and a PPR-DNA cleavage domain fusion protein.

ZFN (zine-finger nuclease) is an artificial nuclease prepared by linking a DNA cleavage domain derived from a nuclease domain of a restriction enzyme or the like to a zinc-finger repeat that specifically recognizes a target sequence and binds thereto. ZFN is one example of the genome editing protein molecule that itself recognizes a target sequence in a genome. The genome editing technique with a ZEN per se is widely known as a first-generation genome editing method (see, for example, Osakabe Y. et al. (2015 March). Genome editing with engineered nucleases in plants. Plant Cell Physiol. 56 (3): 389-400; and Wijshake T. et al. (2014 October). Endonucleases: new tools to edit the mouse genome. Biochim Biophys Acta. 1842 (10): 1942-1950.). ZFN is commonly designed by linking about three units of zinc-finger repeats each recognizing three bases, such that a target sequence of about 18 bases is recognized. As the DNA cleavage domain, a nuclease domain of the restriction enzyme FokI is most commonly utilized. Usually, the C-terminus of the zine-finger domain is linked to the N-terminus of the DNA cleavage domain. In cases where the DNA cleavage domain employed is of a type which produces the DNA cleavage activity in a dimerized form similarly to the nuclease domain of FokI, two ZFNs recognizing two different DNA strands may be used in combination. By using such a pair of ZFNs, a DNA double-strand can be cleaved between two target sequences. In such cases, the target sequences to be recognized by the pair of ZFNs need to be set such that an interval of about several base pairs is appropriately present therebetween.

When a DNA double-strand break is produced in a filamentous fungal genome, repair by non-homologous end-joining (NHEJ) occurs at the double-strand break site. During this process, deletion or addition of one or more bases occurs with high frequency. As a result, a mutation such as a frameshift or stop codon is produced, resulting in modification of the genome such as disruption of the target gene. By allowing a double-stranded DNA fragment to coexist with the DNA double-strand break portion, the DNA fragment can be knocked into the break site.

TALEN (transcription activator-like effector nuclease) is a second-generation genome editing tool using, as a DNA-binding domain, a TAL effector protein of the plant pathogenic bacterial genus *Xanthomonas*, which is linked to a nuclease domain derived from the restriction enzyme FokI or the like. The TAL effector protein has repeated sequence units each consisting of 34 amino acids, and the sequence of each unit recognizes one base. The number of the repeat units corresponds to the chain length of the target sequence. The DNA-binding domain of TALEN is commonly designed such that it recognizes a target sequence of about 18 bases. The method of designing the DNA-binding domain of TALEN is well known (for example, Bogdanove & Voytas. Science 2011, 333 (6051). 1843-1846), and design tools therefor are also known (for example, TAL Effector Nucleotide Targeter 2.0 provided by Cornell University: tale-nt.cac.cornell.edu). TALEN is also one example of the genome editing protein molecule that itself recognizes a target sequence in a genome. In cases where the DNA cleavage domain employed is of a type which produces the DNA cleavage activity in a dimerized form similarly to the nuclease domain of FokI, two TALENs recognizing different DNA strands may be used in combination. By using such a pair of TALENs, a DNA double-strand can be cleaved between two target sequences. In such cases, the target sequences to be recognized by the pair of TALENs need to be designed such that an interval of about 14 to 20 base pairs is appropriately present therebetween. Also in cases where TALEN is used, disruption of a target gene, knock-in of a DNA fragment, or the like can be carried out by non-homologous end-joining at a double-strand break site.

A PPR (pentatricopeptide repeat) protein is a nucleic acid-binding protein discovered in a plant (see, for example. JP 2013-128413 A). A PPR protein has a structure with ten and several consecutive PPR motifs each consisting of 35 amino acids, and each motif corresponds to a base in a one-to-one manner. Thanks to the progress of analysis of the nucleic acid recognition codes of PPRs, designing of a protein that specifically binds to a desired nucleic acid sequence has become possible. A PPR-DNA cleavage domain fusion protein, in which a DNA cleavage domain such as the nuclease domain of the restriction enzyme FokI is linked to a PPR protein, can also be regarded as an artificial nuclease as one example of a genome editing protein molecule. Similarly to ZFNs or TALENs, in cases where the DNA cleavage domain employed is of a type which produces the DNA cleavage activity in a dimerized form, two PPR-DNA cleavage domain fusion proteins recognizing different DNA strands are used in combination as a pair of the fusion proteins.

The complex containing a Cas9 protein and a guide RNA is one example of the complex containing a protein molecule having a DNA cleavage activity and a guide nucleic acid molecule that recruits the protein molecule into a target sequence portion in a genome. The complex produces a DNA double-strand break at a particular site within the target sequence. The genome editing technique utilizing a Cas9 protein and a guide RNA is the third-generation genome editing technique known as the CRISPR/Cas system (see, for example, Gaj T. et al. (2016 December). Genome-Editing Technologies: Principles and Applications. Cold Spring Harb Perspect Biol. 8 (12); and Singh V. et al. (2017 January). Exploring the potential of genome editing CRISPR-Cas9 technology. Gene. 599:1-18.). This technique per se is also well known, and various kits and design tools therefor are known. In the present invention, expression of a polynucleotide(s) encoding a Cas9 protein and a guide RNA in a filamentous fungal cell is not carried out, but a complex containing a Cas9 protein and a guide RNA is directly introduced into a filamentous fungal cell.

The Cas9 protein may be a protein derived from any bacterium. In known CRISPR/Cas systems, Cas9 derived from *Streptococcus pyogenes* is commonly used, and may also be preferably used in the present invention. The Cas9 protein can be obtained by expression and recovery from various known Cas9 expression vectors using an appropriate host cultured cells. A commercially available Cas9 protein may also be used.

As the guide RNA, a single-stranded RNA having a structure in which a chimeric sequence of a short CRISPR RNA (crRNA) and a trans-activating crRNA (tracrRNA) is linked to the 3'-side of the same sequence as the target sequence (except that U is placed instead of T) in the genome may be used. Such a single-stranded RNA can be easily prepared by conventional chemical synthesis. As the chimeric sequence, those used for known CRISPR/Cas systems may also be preferably used in the present invention. The RNA sequence shown in SEQ ID NO: 2 in SEQUENCE LISTING is a chimerie sequence of a short CRISPR RNA (crRNA) and a trans-activating crRNA commonly used when a Cas9 derived from *Streptococcus pyogenes* is used.

The target sequence employed as the guide RNA may be a sequence of about 17 to 25 bases, for example, about 19 to 22 bases, typically about 19 to 20 bases, adjacent upstream of an appropriate PAM (protospacer adjacent motif) sequence in the genome sequence of the filamentous fungus to be subjected to the genome editing. The PAM sequence varies depending on the species and the type of the bacterium from which the Cas9 employed is derived. In cases of the Cas9 derived from *Streptococcus pyogenes* type II, which is most commonly used in known CRISPR/Cas systems, the PAM sequence is 5'-NGG (N represents A. T. G, or C). Other examples of the PAM sequence include 5'-CCN for the Cas9 derived from *Streptococcus solfataricus* type I-A1, 5'-TCN for the Cas9 derived from *Streptococcus solfataricus* type I-A2, and 5'-TTC for the Cas9 derived from *Haloquadratum walsbyi* type I-B. Various other examples are also known.

In the genome of a filamentous fungal cell to which the complex containing the Cas9 protein and the guide RNA is directly introduced, double-strand break of the target sequence occurs between the third and fourth bases positioned upstream of the PAM sequence. In the setting of the target sequence of the guide RNA, first, the sequence of the target gene or target region to be edited may be searched for an appropriate PAM sequence, and adjacent sequences positioned upstream thereof may be selected as candidate sequences. From the candidate sequences, a sequence that has less number of similar sequences in the genome sequence of the filamentous fungus to be edited may be finally selected as a target sequence. By selecting a sequence such that no sequences highly identical thereto are found in the genome and employing it as the target sequence, DNA cleavage by the Cas9 protein at non-target sites (off-target cleavage) can be reduced.

The complexes containing a nickase-modified Cas9 protein and each of a pair of guide RNAs means two kinds (a pair) of complexes in each of which one of two guide RNAs is associated with a nickase-modified Cas9 protein. The nickase-modified Cas9 protein is a modified protein in which one of the two cleavage domains originally contained in the Cas9 protein is inactivated, and the protein cleaves one of the two strands of DNA at the target site. Thus, for cleavage of both strands of DNA, it is necessary to use the nickase-modified Cas9 molecules in combination with two kinds (a pair) of guide RNAs recognizing a target sequence in one strand of DNA and another target sequence in the other strand, respectively. The complexes are usually designed such that the interval between the target sequences recognized by the pair of guide RNAs is not more than one hundred and several ten base pairs, or not more than several ten base pairs. The double-nicking method using a nickase-modified Cas9 protein is a technique developed for the purpose of reducing off-target cleavage by known CRISPR/Cas systems. Also in the genome editing protein direct introduction method of the present invention, reduction of the off-target cleavage can be expected by the use of a nickase-modified Cas9 protein.

Nickase-modified Cas9 per se is known. Known examples of particularly common nickase-modified Cas9 include a Cas9 mutant in which the D10A mutation (substitution from aspartic acid to alanine at the 10th position) is introduced in the RuvC1 nuclease domain, and a Cas9 mutant in which the H840A mutation (substitution from histidine to alanine at the 840th position) is introduced in the HNH nuclease domain. Both of these are applicable to the present invention. In the D10A mutant, the ability to cleave the DNA strand in which the target sequence is present (the strand opposite to the strand with which the guide RNA hybridizes) is lost, and only the strand with which the guide RNA hybridizes is cleaved. In the H840A mutant, the ability to cleave the strand with which the guide RNA hybridizes is lost, and only the strand in which the target sequence is present is cleaved.

The complex containing a nickase-modified or null mutant Cas9 protein to which a deaminase is linked and a guide RNA is one example of the complex containing a protein molecule having a base conversion activity and a guide nucleic acid molecule that recruits the protein molecule into a target sequence portion in a genome. The null mutant Cas9 protein is a mutant in which both of the two cleavage domains contained in the wild-type Cas9 protein are inactivated. It can be prepared by, for example, introducing both of the D10A mutation and the H840A mutation described above.

In recent years, as a new genome editing technique based on the CRISPR/Cas system, a technique for altering a base(s) without producing a DNA double-strand break has also been developed (see, for example, Nishida et al., Science. 2016 Sep. 16; 353 (6305). DOI: 10.1126/science.aaf8729; WO 2015/133554; and Komor et al., Nature 533, 420-424, 19 May 2016). In this technique, a fusion protein in which a deaminase is linked to a Cas9 protein mutant whose at least one DNA cleavage domain is inactivated (nickase-modified or null mutant Cas9 protein) is expressed together with a guide RNA in a cell. After formation of a complex containing the deaminase-mutant Cas9 and the guide RNA in the cell, the guide RNA hybridizes with the complementary strand of the target sequence, and alteration of a base(s) occurs in one of the DNA double-strands due to the activity of the deaminase, causing a mismatch(es) in the DNA double-strand. During the repair process for the mismatch(es), introduction of various mutations into the genome occurs by alteration of the other base(s) in a manner in which the altered base(s) is/are retained, by conversion into still another/other base(s) at the mismatched portion(s), and/or by occurrence of deletion and/or insertion of one or more bases. This technique can be applied also to the present invention to introduce a mutation such as alteration of a base(s), by directly introducing a complex containing a nickase-modified or null mutant Cas9 protein to which a deaminase is linked and a guide RNA into a filamentous fungal cell.

It is known that this technique, which does not produce a DNA double-strand break, allows control of the editing site (the site where the mutation is to be produced) according to the type of the Cas9 protein mutant used, the size of the target sequence, and the like. For example, when the D10A mutant is employed as the mutant Cas9 and activation-induced cytidine deaminase (AID) is employed as the deaminase, cytosine base(s) in the region of 2 to 5 bases from the 5'-end of the target sequence is/are converted to uracil base(s) (equivalent to conversion of cytosine to thymine in terms of genetic information) irrespective of the chain length of the target sequence. As a result of action of the repair mechanism on the thus produced mismatch(es) in the double-stranded DNA as described above, the genetic information can be altered to a base(s) different from the original base(s).

Examples of the deaminase other than cytidine deaminase include adenosine deaminase (which converts adenine to hypoxanthine) and guanosine deaminase (which converts guanine to xanthine). Also by use of these deaminases, the genetic information can be stably altered to a base(s) different from the original base(s) by, for example, conversion to another/other base(s) in the mismatched portion(s).

The complex containing a Cpf1 protein and a guide RNA is one example of the complex containing a protein molecule having a DNA cleavage activity and a guide nucleic acid molecule that recruits the protein molecule into a target sequence portion in a genome. This complex produces a DNA double-strand break at a particular site within the target sequence. As the guide RNA, similarly to those used in known CRISPR/Cas systems, a single-stranded RNA having a structure in which a chimeric sequence of crRNA and tracrRNA is linked to the 3'-side of the target sequence may be used. Unlike a Cas9 protein, a Cpf1 protein produces a cleaved site with a protruding end. However, similarly to CRISPR/Cas systems, both strands of a double-stranded DNA can be cleaved with one kind of Cpf1-guide RNA complex. See, for example, Yamano et al., Cell. Volume 165, Issue 4, p 949-962, 5 May 2016.

The direct introduction of the genome editing protein molecule or complex into a filamentous fungal cell may be carried out, as described below in the Examples, by preparing protoplasts from filamentous fungal cells, and then adding the genome editing protein molecule or complex into a solution of the protoplasts to allow incorporation of the genome editing protein molecule or complex into the protoplasts. The protoplast solution can be prepared by a conventional method using a filamentous fungal cell wall-lysing enzyme such as Yatalase.

In the direct introduction of the genome editing protein molecule or complex, the density of the filamentous fungal protoplast and the concentration of the genome editing protein molecule or complex used may be appropriately set according to the filamentous fungus used, the type of the genome editing protein molecule or complex used, and the like. In cases where a genome editing protein complex involving a CRISPR/Cas system is used, efficient editing of the genome is possible by using not less than about 10 μg of Cas9 protein with respect to about $10^6$ filamentous fungal protoplasts.

Descriptions are given below in order from the first mode.

In the first mode of the present invention, a genome editing protein molecule or complex for a target gene is directly introduced into a cell of an *Aspergillus* fungus, to edit a desired target gene. The most typical embodiment in the first mode is disruption of the target gene by DNA double-strand break or base conversion.

As described above, the *Aspergillus* fungus is preferably a koji fungus, more preferably *Aspergillus oryzae*. The genome editing protein molecule or complex may be either a molecule or complex which cleaves DNA, or a molecule or complex which alters a base(s) without producing a DNA double-strand break. Accordingly, specific examples of the genome editing protein molecule or complex that can be used in the first mode include all specific examples described above.

An *Aspergillus* fungal strain whose target gene is edited may be obtained by screening based on a phenotype that is manifested as a result of the editing. In cases where the target gene is disrupted as a result of the editing, positive selection of the edited strain (disrupted strain) can be carried out by employing, as the target gene, a sensitivity gene such as a drug sensitivity gene or a metabolic analog substance sensitivity gene. Such a strain having a disrupted sensitivity gene can be selected as a strain that acquired resistance to a drug or a metabolic analog substance.

Specific examples of such a sensitivity gene include the following metabolic analog substance sensitivity genes.

pyrG Gene (AO090011000868)

This gene encodes an enzyme that converts 5-fluoroorotic acid (5-FOA), which is an analog of orotic acid, an intermediate metabolite of the uracil biosynthetic pathway, to 5-fluorouridine phosphate. After disruption of this gene, the cell can grow even in the presence of 5-FOA. The selection medium can be prepared with a 5-FOA concentration of about 0.1 mg the 0.1 mM to 10 mM.

SC Gene (AO090020000349)

This gene encodes ATP sulfurylase. After disruption of this gene, the cell can grow even in the presence of sodium selenate. The selection medium can be prepared with a cerulenin concentration of about 0.01 to 1 mM.

niaD Gene (AO090012001035)

This gene encodes nitrite reductase. After disruption of this gene, the cell can grow even in the presence of chloric acid. The selection medium can be prepared with a sodium chlorate concentration of about 0.05 to 1 M.

ptrA Gene (AO090003000090)

This gene encodes a thiamine-synthesizing enzyme. After disruption of this gene, the cell can grow even in the presence of pyrithiamine. The selection medium can be prepared with a pyrithiamine concentration of about 0.2 to 100 ppm.

The candidate genome-edited strain obtained by the screening with the selection medium may be subjected, if desired, to analysis of the genome sequence around the edited site for confirmation of the fact that modification of the genome occurred in the desired target site.

The second mode of the present invention is a method of editing a filamentous fungal genome by knock-in. In this method, a genome editing protein molecule or complex for an arbitrary target region in a genome, and a desired DNA fragment, are directly introduced into a filamentous fungal cell. The genome editing protein molecule or complex employed needs to have a DNA cleavage activity for production of a DNA double-strand break. Accordingly, among the specific examples of the genome editing protein molecules and complexes described above, those that may be used in the second mode include a pair of TALEN proteins; a pair of ZFN proteins; a complex containing a Cas9 protein and a guide RNA; and complexes containing a nickase-modified Cas9 protein and each of a pair of guide RNAs.

The second mode is applicable to a wide range of filamentous fungi. Although the filamentous fungi are not limited, *Aspergillus* fungi are preferred; koji fungi are more preferred; and *Aspergillus oryzae* is especially preferred.

The DNA fragment to be knocked into the filamentous fungal genome is preferably a DNA fragment containing a marker gene fragment. When necessary, a promoter sequence may also be included. In cases where the DNA fragment is to be knocked-in downstream of the transcription start site in a certain gene region, the promoter sequence may be omitted. In cases where knock-in genome editing is carried out for an animal cell or plant cell, the knock-in DNA fragment needs to have at its ends a 5'-homologous region and a 3'-homologous region having the same sequences as the upstream region and the downstream region of the target site, and the DNA fragment needs to be inserted into a DNA double-strand break site by homologous recombination. In contrast, in cases of a filamentous fungal cell, such homologous regions do not need to be included in the DNA fragment since the cell has high non-homologous recombination activity.

The marker gene to be included in the knock-in DNA fragment may be selected such that positive screening for a strain having the DNA fragment knocked therein can be carried out based on the genetic background (drug resistance, auxotrophy, and/or the like) of the parent filamentous fungal strain used. Examples of such a marker gene include drug resistance genes, and genes that complement auxotrophy. Fluorescent protein genes and the like can also be used as the marker gene. Specific examples of such genes include the metabolic analog substance sensitivity genes described above, and aureobasidin resistance genes, bleomycin resistance genes, and carboxin resistance genes.

The DNA fragment and the genome editing protein molecule or complex may be introduced into the filamentous fungal cell at the same time, or one of these may be introduced first. Usually, the DNA fragment and the genome editing protein molecule or complex are added to a protoplast solution, and they are reacted at the same time for a certain length of time to allow their incorporation into protoplasts.

As described above, since filamentous fungal cells have high non-homologous recombination activity, a knock-in DNA fragment is inserted, at a certain frequency, into a site other than the target cleavage site of the genome editing protein molecule or complex. In order to perform efficient screening for a genome-edited strain in which the knock-in occurred at the target cleavage site, it is preferred to disrupt a gene in the filamentous fungal genome by the knock-in, and to carry out, in addition, screening for a phenotype caused by the gene disruption. The knock-in genome editing experiment in the following Examples is one example of such a process, wherein a knock-in site was set such that the wA gene, which is involved in biosynthesis of a spore pigment, was disrupted, and wherein screening for a knock-in-edited strain was carried out by combination of selection based on auxotrophy (using a uracil auxotrophic mutant strain as a parent strain) and selection based on the spore (colony) color. Occurrence of knock-in at the target site can also be confirmed by performing PCR analysis of the genome region containing the knock-in target site, and investigating the amplification size.

The third mode of the present invention is a method of simultaneous editing of a plurality of target genes in a filamentous fungal genome. In this mode, a first genome editing protein molecule or complex for a first target gene, and a second genome editing protein molecule or complex for a second target gene, are directly introduced into a filamentous fungal cell. Further, a third genome editing protein molecule or complex for a third target gene, or even more genome editing protein molecules or complexes may be introduced. In cases where the genome editing protein molecule or complex for each target gene employs a pair of molecules or complexes in combination, a total of two pairs of genome editing protein molecules or complexes are used for simultaneously editing two target genes as a consequence.

In this mode, the genome editing protein molecule or complex may be either a molecule or complex which cleaves DNA, or a molecule or complex which alters a base(s) without producing a DNA double-strand break. Accordingly, specific examples of the genome editing protein molecule or complex that can be used in the third mode include all specific examples described above.

In the third mode, it is preferred to employ a gene for which positive selection can be carried out, as one of the target genes. More specifically, it is preferred to employ a sensitivity gene such as a drug sensitivity gene or a metabolic analog substance sensitivity gene as one of the target genes, and to perform editing such that the gene is disrupted. For convenience, the gene for which positive selection can be carried out is referred to as a first target gene. Preferred specific examples of the first target gene in this case are the same as the preferred specific examples of the target gene in the first mode. Even in cases where positive selection cannot be carried out for the resultant of editing of the second target gene, or where the resulting phenotype is not obvious, a candidate strain in which the second target gene is edited can be obtained by performing screening using, as an indicator, modification of the first target gene. After obtaining the candidate strain, the modification of the second target gene may be confirmed by sequencing of the region around the editing target site of the second target gene (and, if desired, the region around the editing target site of the first target gene).

EXAMPLES

The present invention is described below more concretely by way of Examples. However, the present invention is not limited to the following Examples.

Example 1: Genome Editing of Genus Aspergillus by Direct Introduction of Cas9 Protein and the Like Experimental Methods (1) Fungal Strains, Enzyme, and Guide RNA.
Aspergillus oryzae RIB40, RIB128, RIB915, RIB163, and RIBOIS01
Cas9 protein 12.5 μg [4 μg/μl] [derived from Streptococcus pyogenes; manufactured by FASMAC Co., Ltd.]
Single guide RNA for pyrG [3.25 μg/μl]
The single guide RNA (sgRNA) to be used for disruption of the pyrG gene was designed as follows. First, the pyrG gene sequence was searched for PAM sequences (NGG), and sequences upstream thereof (about 19 to 20 bases) were used as candidates of the protospacer sequence (target sequence). The Aspergillus genome was searched for the candidate sequences, and a sequence for which the absence of off-target sequences could be confirmed was employed as a protospacer sequence. In the present experiment, GACTTCCCCTACGGCTCCGAG (SEQ ID NO: 1) in the pyrG gene was used as the protospacer sequence. As the single guide RNA (sgRNA), the sequence in which GUUUUAGAGCUAGAAAUAGCAAGUUAAAAUA-AGGCUAGUCCGUUAUC AACUUGAAAAAGUG-GCACCGAGUCGGUGCUUUU (SEQ ID NO:2) is linked to the 3'-side of the protospacer sequence was used. The full-length sequence of the sgRNA for pyrG is shown in SEQ ID NO:3.
(2) Reagents Used
0.1M Phosphate buffer (pH 6.0)
A mixture of 88 ml of 1M NaH$_2$PO$_4$ and 12 ml of 1 M Na$_2$HPO$_4$ was prepared, and the pH of the mixture was adjusted to 6.0, followed by adding MILLI-Q® water thereto to a final volume of 1 L, and then autoclaving.
1 M Tris-HCl buffer (pH 7.5).
5 M NaCl
1 M CaCl$_2$: 2H$_2$O
0.1 M Phosphate buffer (pH 6.0)
A mixture of 88 ml of 1M NaH$_2$PO$_4$ and 12 ml of 1 M Na$_2$HPO$_4$ was prepared, and the pH of the mixture was adjusted to 6.0, followed by adding MILLI-Q® water thereto to a final volume of 1 L.
0.8 M NaCl/10 mM phosphate buffer (pH 6.0)
A mixture of 160 ml of 5 M NaCl and 100 ml of 0.1 M phosphate buffer was prepared, and then diluted to a final volume of 1 L, followed by autoclaving.

Solution 1

0.8 M NaCl, 10 mM CaCl$_2$, 10 mM Tris-HCl buffer (pH 7.5)

Solution 2

40% (w/v) PEG 4000, 50 mM CaCl$_2$, 10 mM Tris-HCl buffer (pH 7.5)
Protoplast Preparation Solution
To 20 ml of 0.8 M NaCl/10 mM phosphate buffer (pH 6.0). 100 mg of Yatalase (TaKaRa) was added, and the resulting mixture was suspended by vortexing. After the solution became clear, filter sterilization was carried out after attachment to STERIFLIP® 0.22 μm (Merck Millipore).
(3) Media
Koji Fungal Enzyme Production Medium (/L)
After dissolving 20 g of glucose, 1 g of bacto tryptone, 5 g of yeast extract, 1 g of NaNO$_3$, 0.5 g of K$_2$HPO$_4$, 0.5 g of MgSO$_4$·7H$_2$O, and 0.01 g of FeSO$_4$·7H$_2$O in deionized water, the pH was adjusted to 6.0, and the resulting solution was diluted to a final volume of 1 L, followed by autoclaving.
pyrG Selection Medium (/L)
After dissolving 20 g of glucose, 3 g of NaNO$_3$, 0.5 g of KCl, 46.752 g of NaCl, 1 g of KH$_2$PO$_4$, 0.5 g of MgSO$_4$·7H$_2$O, 0.02 g of FeSO$_4$·7H$_2$O, 2.442 g of uridine, and 20 g of agar (7 g in the case of the layering soft agar medium) in deionized water, the pH was adjusted to 6.5, and the resulting solution was diluted to a final volume of 0.9 L, followed by autoclaving. After autoclaving, 100 ml of 0.01 g/ml 5'-fluoroorotic acid (5'-FOA) solution (pH 6.5) sterilized aseptically with a 0.22-μm filter was added thereto. The selection medium for subculture was prepared without using NaCl.

(4) Experimental Procedure

All operations were aseptically carried out in a clean bench. All tools were autoclaved and sufficiently dried before use.
A. Fungal Cell Culture
To 150 ml of the koji fungal enzyme production medium (in a 500-ml baffled flask), a conidial suspension was added to a final concentration of about 1×10$^6$ conidia/ml, and then shake culture was carried out at 30° C., for 17 to 20 hrs at 80 to 100 rpm.
B. Preparation of Protoplast Solution
The cultured fungal cells were collected by filtration using a funnel to which Miracloth was attached.
The collected fungal cells were washed three times with 0.8 M NaCl/10 mM phosphate buffer (pH 6.0).
To 20 ml of the protoplast preparation solution, about 0.5 g of dehydrated fungal cells were added, and the resulting mixture was slowly shaken (at 60 to 80 rpm) at 30° C., for 2 to 3 hr.
In a clean bench, for removal of residues, the fungal cells were subjected to filtration using a 3G (1-3) glass filter to which Miracloth was attached, and a protoplast solution was collected into a 50-ml Falcon tube.
From the top of the Miracloth, 10 ml of 0.8 M NaCl/10 mM phosphate buffer was poured to wash the filter and the like.
The collected protoplast solution was centrifuged at 3000 rpm for 5 min at 4° C.

The supernatant was removed. Thereafter, washing was carried out twice with 10 ml of 0.8 M NaCl/10 mM phosphate buffer.

The number of protoplasts was counted, and the protoplasts were suspended in Solution 1 to a final concentration of 2.4 to $2.0 \times 10^8$/ml.

C. Synthesis and Addition of Ribonucleoprotein (RNP)

Fifty-microliter aliquots of the protoplast solution, prepared by suspending in Solution 1, were dispensed into 2-ml microtubes.

In another tube, sgRNA (6.75 μg/2 μl) and Cas9p (12 μg/3 μl) were mixed together by several times of pipetting, and then left to stand on ice for 15 min to allow their association (the resulting product was provided as an RNP solution).

The RNP solution thereafter was added to the dispensed protoplast solutions.

To each of the resulting mixtures, 12.5 μl of Solution 2 was added.

The resulting mixtures were left to stand on ice for 30 min.

After adding 500 μl of Solution 2, each of the resulting mixtures was mixed, and then left to stand at room temperature for 15 minutes.

D. Layering on Selection Medium

The layering soft agar medium was preliminarily dispensed and warmed at 45° C., and an appropriate amount of the RNP-protoplast solution was added to the medium, followed quickly pouring and layering the resulting mixture on the selection medium.

Culture was performed at 30° C. with saturated humidity for 4 to 5 days.

E. Subculture

After appearance of colonies, the cells were subcultured to the -pyrG selection medium (NaCl-free).

F. Isolation and Storage

Conidia were collected from isolated candidate strains, and then stored in the presence of 30% glycerol at -30° C.

G. Small-Scale Genome Extraction

To an EPPENDORF® tube, 600 μl of a medium was placed, and about 10 μl of the conidial suspension was inoculated.

Culture was carried out overnight with shaking at 37° C.

After centrifugation at 15,000 rpm for 5 min at room temperature, the culture supernatant was removed as much as possible such that fungal cells were not removed.

To the fungal cells, 450 μl of glass beads were added.

After adding thereto 600 μl of Nuclei Lysis Solution of a Wizard Genomic DNA purification kit, the resulting mixture was suspended.

The resulting suspension was vortexed or stirred at 3000 rpm with a shaker for 3 minutes or more.

The suspension was then frozen at -20° C., and then thawed, followed by heating at 65° C., for 5 minutes.

After adding thereto 100 μl of PI buffer (RNase-treated) of a QIAGEN® Plasmid extraction kit, the resulting mixture was suspended.

The reaction was allowed to proceed at room temperature for 15 minutes. (At this time, the solution was observed to confirm that it was slightly cloudy.)

To the fungal cell liquid after the disruption, 200 μl of Protein precipitation Solution was added, and the resulting mixture was stirred.

Centrifugation was carried out at 15,000 rpm for 10 min at room temperature.

To another EPPENDORF® tube, 0.65 ml of the supernatant was transferred, and 0.65 ml of isopropanol was added thereto.

The resulting mixture was cooled at -20° C., for 30 minutes.

Centrifugation was carried out at 15,000 rpm for 30 min at room temperature.

The resulting precipitate was washed by addition of 0.65 ml of 70% ethanol (the same amount as the isopropanol that was added in the prior step) thereto.

Centrifugation was carried out at 15,000 rpm for 10 min at room temperature.

The precipitate was dissolved in 50 μl of TE.

The concentration and the purity of the DNA were investigated.

H. Preparation of Sequencing Template for pyrG by PCR

For PCR, KOD-plus-neo was used. As counted from the 5'-end of the ORF (899 bp) of pyrG as the reference position (first base), primers were designed for the region of -969:-948 (22 bp) and the region of 1973:1993 (23 bp) (the following Table 1). Amplification products of up to about 2961 bp were obtained by PCR.

The PCR reaction was carried out with a total volume of 50 μl containing 5 μl of 10×buffer, 5 μl of dNTPs, 3 μl of MgSO$_4$, 1 μl of Primer A (10 μM), 1 μl of Primer B (10 μM), 1 μl of the template, 1 μl of KOD-plus-neo, and 33 μl of sterile MilliQ water. The PCR cycle conditions were as follows. Denature: 94° C., 2 min. Denature-Annealing-Extension: (94° C., 15 sec-58.2° C., 30 sec-68° C., 3 min) 30 cycles, 68° C., 2 min., 4° C. constant. For purification of the PCR product, a QIAGEN® QIAQUICK® PCR Purification kit was used.

Sequence analysis of each sample was carried out with sequencing primers designed for six regions (Table 1). As counted from the 5'-end of the ORF (899 bp) as the reference position (first base), the primers were designed for the following six regions: -969:-948 (22 bp), 139:1628 (24 bp), 306:325 (20 bp), 624:643 (20 bp), 734:757 (24 bp), and 1973:1993 (23 bp). (The region targeted by the guide RNA in this experiment was 492:515 (24 bp), and the six primers were designed such that they were relatively symmetrically positioned around this region.)

TABLE 1

| Primer name | Sequence (5'→3') | SEQ ID NO: | Use |
|---|---|---|---|
| pyrGfullA | GGGAGACAAAGCTAACAACGTC | 4 | Template amplification, Sequence analysis |
| pyrGfullB | GTATGCACAGTCAGGACTCCA | 5 | Template amplification, Sequence analysis |

TABLE 1-continued

| Primer name | Sequence (5'→3') | SEQ ID NO: | Use |
|---|---|---|---|
| pyrGseqA | GCCCTTGCAGAGAAGCACAA | 6 | Sequence analysis |
| pyrGseqB | AGGTGACGTGTCGAGACGAA | 7 | Sequence analysis |
| pyrGperA | CTGCTGGATTTGGCTGACCGTATG | 8 | Sequence analysis |
| pyrGperB | GTTTGGTACTGCTGTCCCAGCTTG | 9 | Sequence analysis |

I. Sequence Analysis

Sequence analysis was carried out by outsourcing to FASMAC Co., Ltd. For the analysis, [Applied Biosystems 3130xl Genetic Analyzer, and Applied Biosystems 3730xl DNA Analyzer] were used as sequencers, and [Applied Biosystems Big Dye Terminator V3.1] was used as a reaction reagent.

<Results>

(1) Genome Editing Experiment with RIB40 Strain

First, whether genome editing is possible by the present method was studied using RIB40, which is a wild strain of koji fungus.

The enzyme encoded by the pyrG gene has an activity that converts 5-fluoroorotic acid (5-FOA), which is an analog of orotic acid, an intermediate metabolite of the uracil biosynthetic pathway, to 5-fluorouridine phosphate. Since 5-fluorouridine phosphate strongly inhibits thymine synthetase, a wild strain having the normal function of the pyrG gene cannot grow in the presence of 5-FOA. When the enzyme activity is lost by disruption of the pyrG gene, growth in the presence of 5-FOA becomes possible. Thus, whether the pyrG gene could be disrupted by the introduction of the sgRNA for pyrG disruption and Cas9p can be confirmed using growth on a 5-FOA-containing medium as an indicator.

When $1.8 \times 10^6$ protoplasts of RIB40 mixed with a buffer (10 mM Tris-HCl, 200 mM KCl, 1 mM DTT, 10 mM MgCl$_2$, 3 μl of 20% glycerol (pH 7.5), and 2 μl of DEPC water) (−Cas9p, −sgRNA) were plated and cultured on the pyrG selection medium (containing uridine and 5-FOA), utilization of 5-FOA in the uracil synthetic system occurred, leading to production of the lethal action. Thus, colonies did not grow (FIG. 1A). On the other hand, when protoplasts of RIB40 mixed with the RNP solution (+Cas9p, +sgRNA; 6.75 μg of sgRNA and 12 μg of Cas9p were used in a reaction system of 55 μl) were plated on the −pyrG selection medium, growth of colonies could be found (FIG. 1C). From a total of $1.0 \times 10^7$ protoplasts mixed with the RNP solution, 289 pyrG-disrupted strains could be obtained.

(2) Sequence Analysis of Candidate RIB40 Genome-Edited Strains

For 24 strains randomly selected from the 289 candidate strains, sequence analysis of the region around the ORF of the pyrG gene was carried out. The results of sequence analysis of the region around the sgRNA recognition sequence are shown in Table 2. Among the 24 strains, 11 strains showed a one-base deletion at the same site. Further, 6 strains showed deletions of 10 to 300 bases, and 7 strains showed deletions of 1000 to 1800 bases.

TABLE 2

| Strain ID reference | Mutation | Sequence CGGCCGAGgacttcccctacggctccgagAGGGGCCTTTTGATCCTTGCGG |
|---|---|---|
| GeKS1-2 | 1 bp DEL | CGGCCGAGGACTTCCCCTACGGCTC-GAGAGGGGCCTTTTGATCCTTGCGG |
| GeKS1-6 | 1 bp DEL | CGGCCGAGGACTTCCCCTACGGCTC-GAGAGGGGCCTTTTGATCCTTGCGG |
| GeKS1-10 | 1 bp DEL | CGGCCGAGGACTTCCCCTACGGCTC-GAGAGGGGCCTTTTGATCCTTGCGG |
| GeKS1-19 | 1 bp DEL | CGGCCGAGGACTTCCCCTACGGCTC-GAGAGGGGCCTTTTGATCCTTGCGG |
| GeKS1-25 | 1 bp DEL | CGGCCGAGGACTTCCCCTACGGCTC-GAGAGGGGCCTTTTGATCCTTGCGG |
| GeKS1-26 | 1 bp DEL | CGGCCGAGGACTTCCCCTACGGCTC-GAGAGGGGCCTTTTGATCCTTGCGG |
| GeKS1-28 | 1 bp DEL | CGGCCGAGGACTTCCCCTACGGCTC-GAGAGGGGCCTTTTGATCCTTGCGG |
| GeKS1-30 | 1 bp DEL | CGGCCGAGGACTTCCCCTACGGCTC-GAGAGGGGCCTTTTGATCCTTGCGG |
| GeKS1-31 | 1 bp DEL | CGGCCGAGGACTTCCCCTACGGCTC-GAGAGGGGCCTTTTGATCCTTGCGG |
| GeKS1-32 | 1 bp DEL | CGGCCGAGGACTTCCCCTACGGCTC-GAGAGGGGCCTTTTGATCCTTGCGG |
| GeKS1-35 | 1 bp DEL | CGGCCGAGGACTTCCCCTACGGCTC-GAGAGGGGCCTTTTGATCCTTGCGG |
| GeKS1-17 | 10 bp DEL | CGGCCGAGGACTTCCC----------GAGAGGGGCCTTTTGATCCTTGCGG |
| GeKS1-8 | 16 bp DEL | CGGCCGAGGACTTCCCCTACG----------------TTTGATCCTTGCGG |
| GeKS1-14 | 12 bp DEL | CGGCCGAGGACTTCCCCTACGGCT------------TTTTGATCCTTGCGG |
| GeKS1-21 | 26 bp DEL | CGGCCGAGGACTTCCCCTA--------------------------TTGCGG |

TABLE 2-continued

| Strain ID reference | Mutation | Sequence CGGCCGAGgacttcccctacggctccgagAGGGGCCTTTTGATCCTTGCGG |
|---|---|---|
| GeKS1-3 | 62 bp DEL | ---------------------------GAGGGGCCTTTTGATCCTTGCGG |
| GeKS1-12 | 222 bp DEL | CGGCCGAGGACTTCCCCTA------------------------------- |
| GeKS1-15 | 1018 bp DEL | -------------------------GAGAGGGCCTTTTGATCCTTGCGG |
| GeKS1-27 | 1291 bp DEL | CGGCCGAGGACTTCCCCTACGGCTC------------------------ |
| GeKS1-29 | 1369 bp DEL | CGGCCGAGGACTTCCCCTACGGCTC------------------------ |
| GeKS1-33 | 1436 bp DEL | CGGCCGAGGACTTCCCCTACGGCTC------------------------ |
| GeKS1-18 | 1376 bp DEL | ---------------------------------------------TGCGG |
| GeKS1-5 | 1742 bp DEL | -------------------------------------------------- |
| GeKS1-7 | 1781 bp DEL | -------------------------------------------------- |

*In the underlined portion of the reference sequence, the lower-case letters indicate the recognition sequence of the gRNA, and the boldface letters indicate the PAM sequence.

(SEQ ID NOS: 17, 18 (GeKS1-2, 6, . . . , 35) 10 20, 21, 22; 23, 24, 25, and 26(GeK51-2) respectively).

(3) Study on Amount of Cas9 Protein Used

Figure 2:
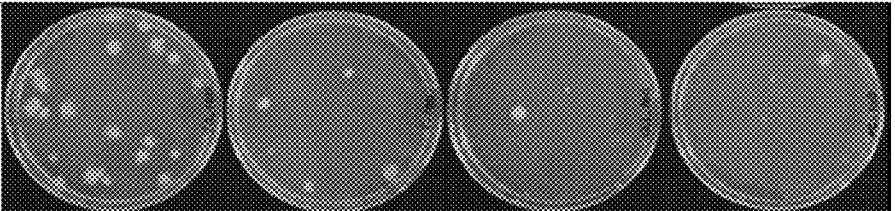
FIG. 2 shows the result of a study on the amount of the Cas9 protein used in the genome editing method by direct introduction of the Cas9 protein-guide RNA complex of Example 1.

The amount of the Casa protein used was studied. RIB40 was used as a host. The amount of the Cas9 protein mixed with protoplasts ($1.8 \times 10^6$ protoplasts) in the study was 10 µg, 1 µg, 0.1 µg, or 0 µg/55 µl. The results are shown in FIG. 2. It was thought that, for efficient genome editing of the koji fungus, use of about 10 µg or more of Cas9 protein with respect to about $10^6$ protoplasts is desirable.

(4) Genome Editing Test with Practically Used Strains

Figure 3:
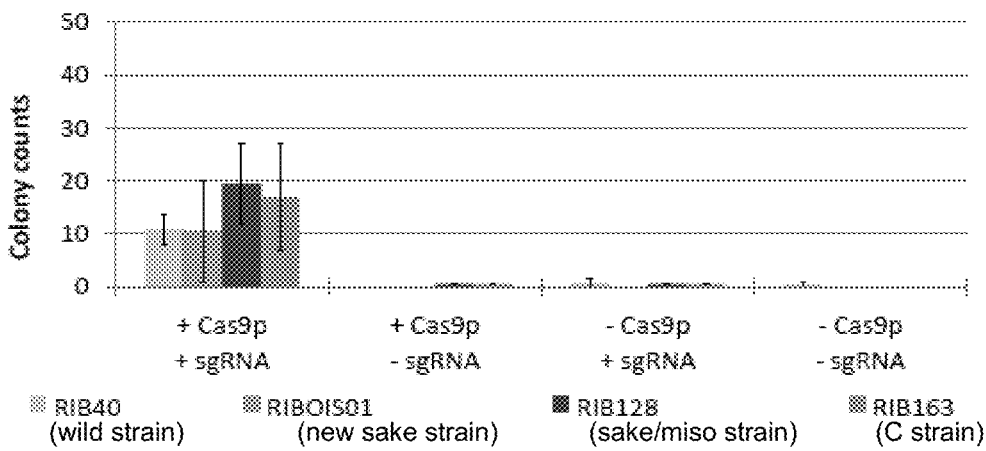
FIG. 3 shows the result of a study to investigate whether or not genome editing (disruption of the pyrG gene) is possible by direct introduction of the Cas9 protein-guide RNA complex, using the representative practical strains of *Aspergillus oryzae* RIBOIS01 (new sake strain). RIB128 (sake/miso strain), and RIB163 (C strain). In all strains, the pyrG gene was disrupted, and strains capable of growing on the 5-FOA-containing selection medium were obtained, confirming that genome editing is possible by this method.

Whether genome editing by the present method is possible or not was investigated for koji fungal strains other than RIB40. RIBOIS01 (new sake strain), RIB128 (sake/miso strain), and RIB163 (C strain), which are representative strains as practically used strains, were used. Based on the result of 1. (3) described above, the amount of the Cas9 protein was set to 10 µg/55 µl. As a result, as shown in FIG. 3, the pyrG gene could be disrupted by the present method also in the koji fungal strains other than RIB40. Thus, it could be confirmed that the method enables genome editing also in the koji fungal strains other than RIB40.

Example 2: Genome Editing of Filamentous Fungus by Knock-In Using Direct Introduction Method with Cas9 Protein and the Like Experimental Methods, and Results (1) Preparation of pyrG DNA Fragment for Knock-in As a template, chromosomal DNA of the wild strain RIB40 of *Aspergillus oryzae* was used in all cases. As primers, pyrGfullA (SEQ ID NO:4) and pyrGfullB (SEQ ID NO:5) were used.

TABLE 3

Composition of PCR reaction liquid (total liquid volume, 50 µl)

| Reagent | Amount used | Final concentration |
|---|---|---|
| Sterile water | 11.5 µl | |
| 2 × PCR Buffer for KOD-FX-Neo | 25 µl | 1 × |
| 2 mM dNTPs | 10 µl | 200 µM |
| Primer (10 µM) | 0.75 µl × 2 | 0.15 µM |
| Template (*A. oryzae* chromosomal DNA solution) | 1 µl | 50 ng |
| KOD-FX-neo DNA polymerase | 1 µl | 1 U |

In a 0.2-ml PCR tube, 50 µl of the above-described reaction liquid was prepared by blending, and the tube was placed in a DNA thermal cycler, followed by performing PCR with the following temperature settings.

[94° C., 2 minutes]×1 cycle
[98° C., 10 seconds-58.2° C., 30 seconds-68° C., 1 minute 30 seconds]×30 cycles
[68° C., 2 minutes-4° C., O/N]×1 cycle In a 1.5-ml microtube, 50 µl of the whole PCR reaction liquid was collected, and an equal amount of phenol/chloroform/isoamyl alcohol (25:24:1) (Nippon Gene) was added thereto, followed by stirring the resulting mixture, and then performing centrifugation at 15,000 rpm at 4° C., for 5 min, to obtain a supernatant. To the supernatant collected, 1/10 volume of 3 M sodium acetate solution and 2.5 volumes of 100% ethanol were added, and the resulting mixture was mixed by inversion, followed by leaving the mixture to stand at room temperature for 10 minutes. A precipitate was obtained by centrifugation at 15,000 rpm at 4° C., for 2 min, and then suspended as appropriate in TE solution to adjust the concentration to 6 µg/µl. The resulting solution was provided as a knock-in DNA (pyrG$^{RIB40}$) solution.

(2) Genome Editing by Direct Introduction of Protein and the Like Using Transformation Method As a host koji fungus, the *Aspergillus oryzae* GeKS1-30 strain (an RIB40 genome-edited strain-pyrG; a strain with pyrG functional deficiency caused by the 1-bp deletion shown in Table 2 above, which exhibits uracil auxotrophy) was used. A conidial suspension of this strain was inoculated to a koji fungal enzyme production medium (see 1, for its composition) supplemented with 10 mM uridine.

The same operations as in 1, were carried out until the preparation of the protoplast solution containing $2.4 \times 10^8$ protoplasts/ml and the RNP solution, except that an sgRNA for wA gene disruption was used instead of the sgRNA for pyrG gene disruption. In the sgRNA for wA gene disruption. GAAAGATGCCTCGCAGCTTAT (SEQ ID NO:10) within the wA gene exon 3 was employed as the protospacer sequence, and to the 3'-side of this sequence GUUUUA-GAGCUAGAAAUAGCAAGUUAAAAUAAGGCUAGU-CCGUUAUC AACUUGAAAAAGUGGCACCGAGUCG-GUGCUUUU (SEQ ID NO:2) was linked. The full-length sequence of the sgRNA for wA gene disruption is shown in SEQ ID NO:11.

To 5 µl of the prepared RNP solution of the sgRNA for wA gene disruption, 1 µl of the pyrG$^{RIB40}$ solution (corresponding to 6 µg of DNA) was added, and the resulting mixture was mixed by several times of pipetting, followed by leaving the mixture to stand on ice for 15 min. The resulting mixed solution was provided as an RNP+DNA solution. To 50 µl of the protoplast solution, 6 µl of the RNP+DNA solution was added, and then reaction was carried out by the same method as described in 1., followed by inoculation of 200 µl of the resulting product to a uracil-free soft agar medium (20 g of glucose, 3 g of NaNO$_3$, 0.5 g of KCl, 1 g of KH$_2$PO$_4$, 0.5 g of MgSO$_4$·7H$_2$O, and 0.02 g of FeSO$_4$·7H$_2$O, pH6.5) supplemented with 0.8 M NaCl. The resulting mixture was mixed by inversion, and then layered on a plate of a uracil-free agar medium supplemented with 0.8 M NaCl. Thereafter, culture was carried out at 30° C., until formation of colonies.

Figure 4:
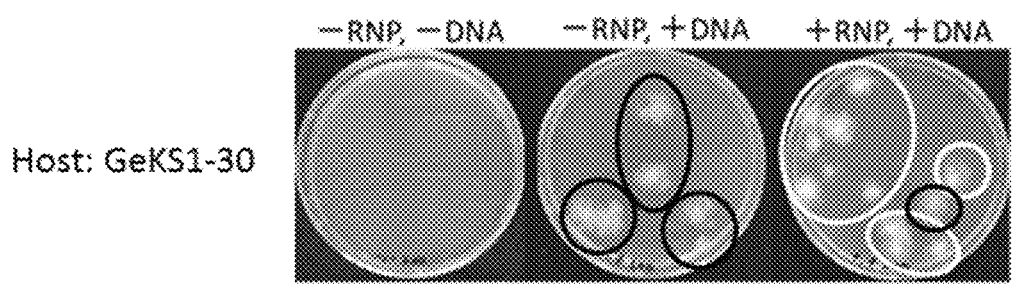
FIG. 4 shows images of colonies obtained as a result of the knock-in experiment that was carried out in Example 2. Using the pyrG function-deficient strain (showing uracil auxotrophy) obtained in Example 1 as a parent strain, a pyrG gene fragment was knocked in by the direct introduction method with the Cas9 protein-guide RNA complex, and then cells were cultured on a uracil-free selection medium. The colonies surrounded by the black lines are green colonies, and the colonies surrounded by the white lines are white colonies.

The culture on the plates to which the RNP and the pyrG$^{RIB40}$ were added resulted in production of an average of 25 candidate strains as white colonies, and an average of 1.7 candidate strains as green colonies. The culture on the plates to which pyrG$^{RIB40}$ alone was added resulted only in production of an average of 12.3 candidate strains as green colonies (FIG. 4, Table 4). In FIG. 4, the colonies surrounded by the black lines are green colonies, and the colonies surrounded by the white lines are white colonies.

TABLE 4

| RNP | DNA (pyrG) | Colony number (n = 3) | |
|---|---|---|---|
| | | White | Green |
| + | + | 25 | 1.7 |
| − | + | 0 | 12.3 |
| − | − | 0 | 0 |

(3) Analysis of Knock-In Candidate Strains by PCR

Figure 5:
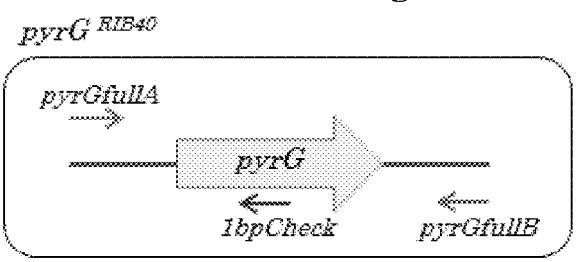
FIG. 5 shows a schematic diagram illustrating the primers designed for PCR analysis of candidate strains having the pyrG gene fragment knocked therein obtained in Example 2.
Figure 5:
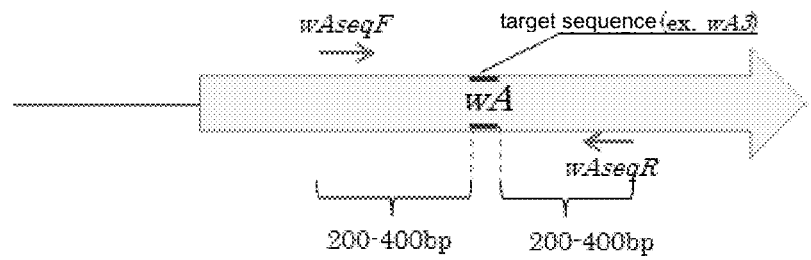

The DNA solution to be used as the template for the PCR was obtained by the same method as in 1., except that a uracil-free liquid medium was used instead of the -pyrG selection liquid medium. In order to investigate the presence or absence of the knock-in, primers wAseqF and wAseqR were designed within ranges of 200 to 400 bp upstream and downstream of the target site (FIG. 5, Table 5), and PCR reaction was carried out using the primers. For the PCR, Taq Hot Start Version [TaKaRa] was used.

TABLE 5

Primers for PCR analysis

| Primer name | Sequence (5'→3') | SEQ ID NO: |
|---|---|---|
| wAseqF | CCTAATCCGGCTCTGGAGAGTGCGT | 12 |
| wAseqR | ATCCTGTCGACATCTCGGCCATAGTACAG | 13 |
| 1bpCheck | TCATCTCCGCAAGGATCAAAAGGCCCCTCTCGG | 14 |

TABLE 6

Composition of PCR reaction liquid (total liquid volume, 50 µl)

| Reagent | Amount used | Final concentration |
|---|---|---|
| Sterile water | 38.25 µl | |
| 10 × PCR Buffer for Taq Hot Start | 5 µl | 1 × |
| dNTP Mixture | 4 µl | 200 µM |
| Primer (10 µM) | 0.75 µl × 2 | 0.3 µM |
| Template (*A. oryzae* chromosomal DNA solution) | 1 µl | 50 ng |
| Taq Hot Start [TaKaRa] polymerase | 0.25 µl | 1 U |

In a 0.2-ml of PCR tube, 50 µl of the above-described reaction liquid was prepared by blending, and the tube was placed in a DNA thermal cycler, followed by performing PCR with the following temperature settings.

Figure 6:
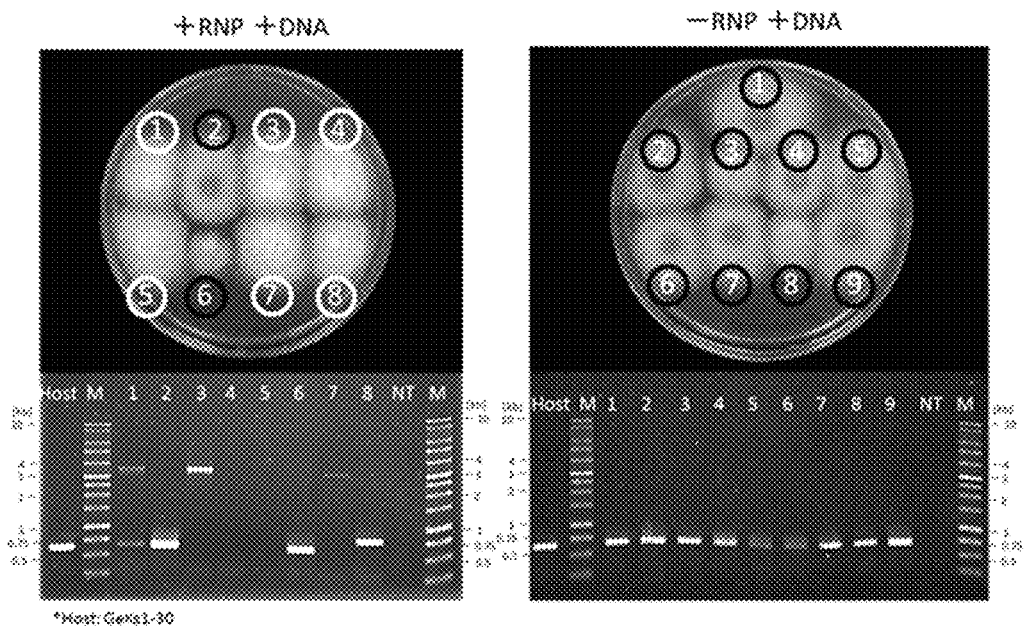
FIG. 6 shows the result of PCR analysis of the candidate strains having the pyrG gene fragment knocked therein obtained in Example 2, which analysis was carried out using the primers designed as shown in FIG. 5.

[94° C., 10 seconds]×1 cycle
[98° C., 10 seconds-66.2° C., 30 seconds-68° C., 1 minute 45 seconds]×30 cycles
[68° C., 2 minutes-4° C., O/N]×1 cycle The resulting PCR reaction liquid was subjected to electrophoresis in 0.8% Agarose S [Nippon Gene]/TAE gel at 100 V for 25 min. As a result, the green strains yielded an amplification product of about 600 bp, and the white strains yielded an amplification product of about 3600 bp (FIG. 6). In FIG. 6, the colonies surrounded by the black circles are green colonies, and the colonies surrounded by the white circles are white colonies. It is suggested that, in the white colonies, the pyrG DNA fragment pyrG$^{RIB40}$ is knocked-in at the target site within the wA gene, in the same orientation as or in the opposite orientation to the wA gene (FIG. 7).

Figure 7:
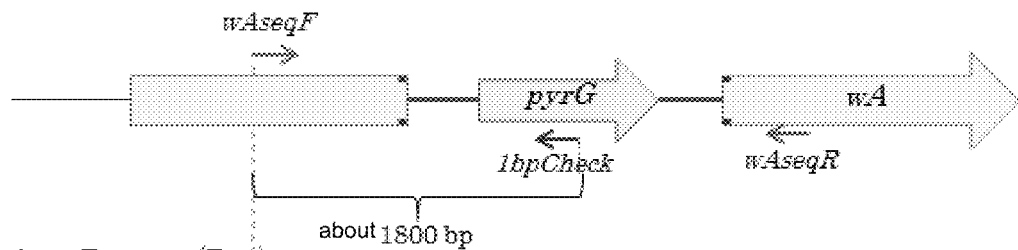
FIG. 7 shows a schematic diagram illustrating primers for analysis of the orientation of the pyrG gene fragment that was knocked into the wA gene.
Figure 7:
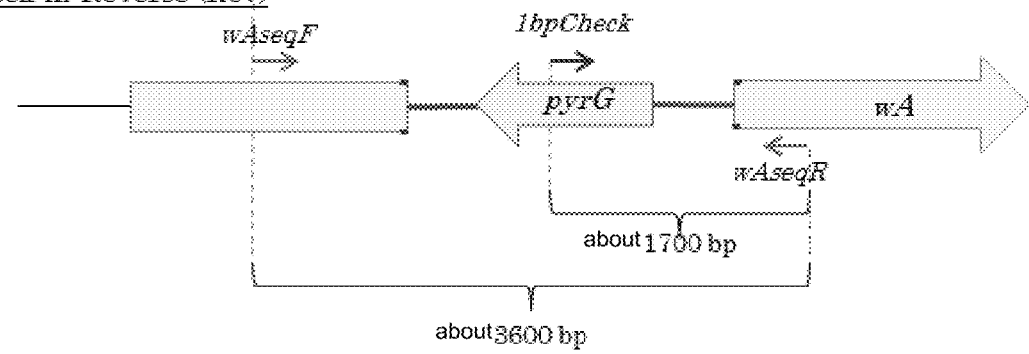

Subsequently, in order to determine the orientation of the pyrG$^{RIB40}$, PCR was carried out using the combination of 1bpCheck, which is a primer designed within the pyrG$^{RIB40}$, and wAseqF and wAseqR, which are the primers used for the confirmation of the knock-in (see Table 5 for the sequences of the primers) (FIG. 7).

PCR was carried out using the reaction liquid having the same composition as described above, but with the following different temperature settings. No. 3 and No. 7, which formed white colonies and yielded single bands in the PCR with the primers wAseqF and wAseqR, were used as templates.

Figure 8:
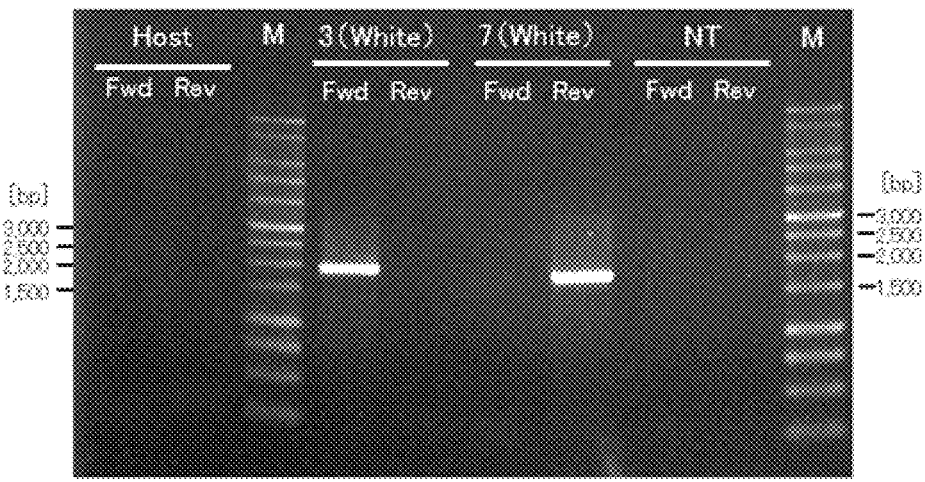
FIG. 8 shows the result of PCR analysis of the orientation of the pyrG gene fragment knocked into the wA gene in white colony strains obtained in Example 2, using the primers designed as shown in FIG. 7.

[94° C., 10 seconds]×1 cycle
[98° C., 10 seconds-66.2° C., 30 seconds-68° C., 1 minute 45 seconds]×30 cycles
[68° C., 2 minutes-4° C., O/N]×1 cycle As a result of electrophoresis of the resulting PCR reaction liquid under the same conditions as described above, No. 3 showed amplification only with the combination of the wAseqF and 1bpCheck primers, and No. 7 showed amplification only with the combination of the 1bpCheck and wAseqR primers (FIG. 8). Thus, it is thought that No. 3 has a pyrG$^{RIB40}$ knocked-in in the same orientation (Forward: Fwd.) as the wA gene, and that No. 7 has a pyrG$^{RIB40}$ knocked-in in the opposite orientation (Reverse: Rev) to the wA gene.

3. Simultaneous Genome Editing of Filamentous Fungus Using Direct Introduction Method with Cas9 Protein and the Like Experimental Methods (1) Fungal Strain, Enzyme, and Guide RNA As a fungal strain, *Aspergillus oryzae* RIB40 was used. The same Cas9 protein as in 1. and 2. was used. As guide RNAs, the sgRNA for pyrG gene disruption used in 1., and the sgRNA for wA gene disruption used in 2., were used.

(2) Genome Editing by Direct Introduction of Protein and the Like Using Transformation Method In the same manner as in 1., a conidial suspension of the RIB40 strain was inoculated to the koji fungal enzyme production medium, to prepare a protoplast solution containing $2.4×10^8$ protoplasts/ml. As RNP solutions, an RNP solution of the sgRNA for pyrG (6.75 μg/2 μl) and the Cas9p (12 μg/3 μl) (pyrG-RNP solution), and an RNP solution of the sgRNA for wA (6.75 μg/2 μl) and the Cas9p (12 μg/3 μl) (wA-RNP solution), were prepared. Each of these solutions was prepared by the same procedure as in 1. To 50 μl of the protoplast solution which was prepared by suspending in Solution 1, 5 μl each of the pyrG-RNP solution and the wA-RNP solution was added, and reaction was carried out by the same method as in 1 (RNP-protoplast solution). To a -pyrG selection soft agar medium, 200 μl of the RNP-protoplast solution was inoculated, and the resulting mixture was mixed by inversion, followed by layering on a plate of a -pyrG selection agar medium. Thereafter, culture was carried out at 30° C., until formation of colonies.

Results

Figure 9:
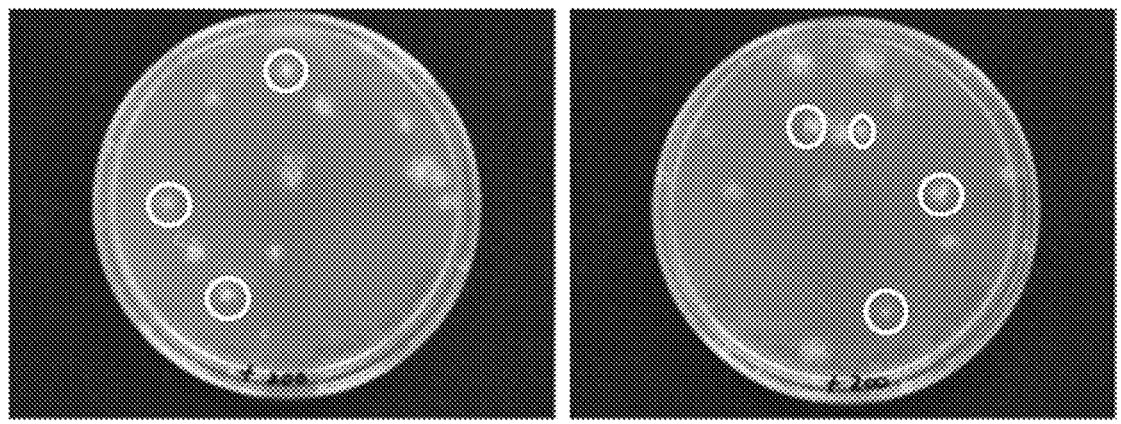
FIG. 9 shows images of colonies obtained as a result of simultaneous disruption of the pyrG gene and the wA gene in a genome by the direct introduction method with the Cas9 protein-guide RNA complex in Example 3. Since a 5-FOA-containing selection medium was used, strains in which the pyrG gene is disrupted can grow. Strains in which the wA gene is also disrupted form white colonies on the medium. The colonies surrounded by the white lines are white colonies.

As a result of the direct introduction of the pyrG-RNP and the wA-RNP into the protoplasts, colonies that were thought to have undergone disruption of not only the pyrG gene, but also the wA gene (white colonies) appeared as shown in FIG. 9. It is thought that the green colonies are colonies which acquired 5-FOA resistance due to disruption of the pyrG gene, but in which the wA gene was not disrupted.

Figure 10:
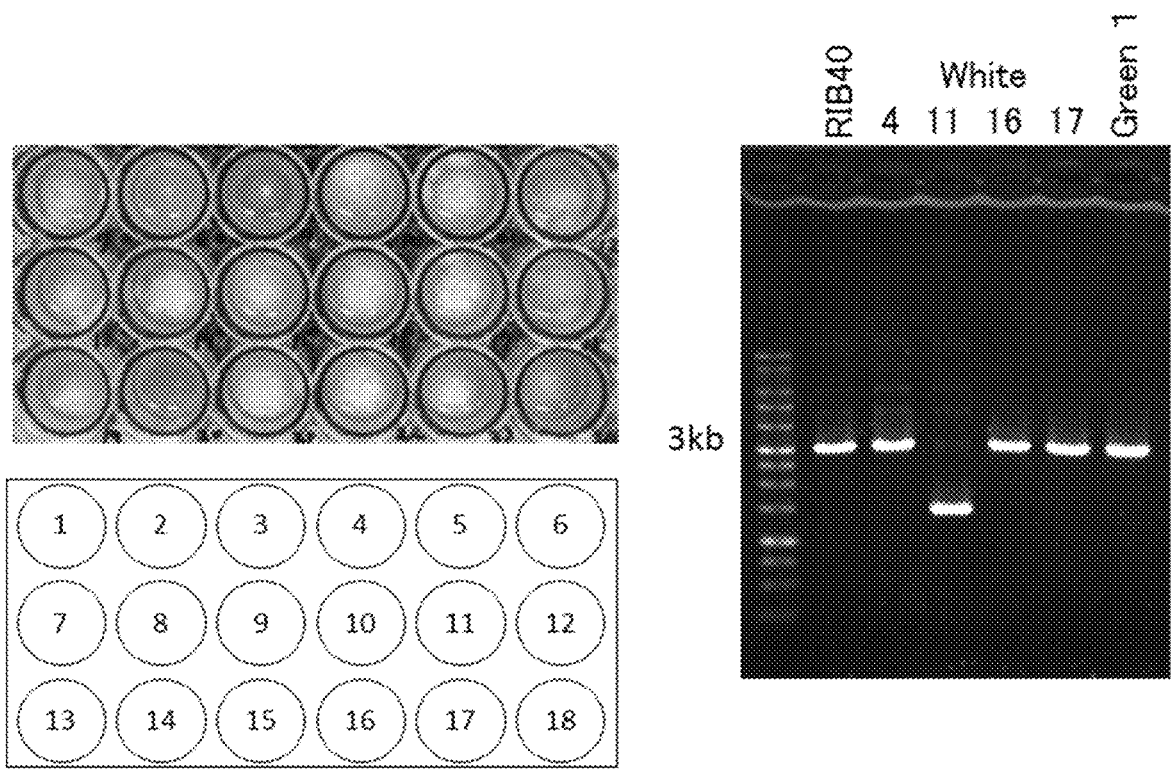
FIG. 10 shows results obtained by further subjecting the 5-FOA-resistant strains obtained in Example 3 to culture in the presence of 5-FOA, and then subjecting resulting white colonies (Nos. 4, 11, 16, and 17) to PCR analysis of the wA gene region to confirm the amplification size.

Strains that acquired 5-FOA resistance by the simultaneous genome editing were cultured again in the presence of 5-FOA. From white colonies (Nos. 4, 11, 16, and 17 in FIG. 10), a wA gene region including the target site was amplified by PCR using the primers pyrGfullA and pyrGfullB described in Table 1, and wAleftA-F and wArightD-R described in the following Table 7. As a result, as shown in FIG. 10, three strains showed bands having the same size. It is thought that No. 11 has a large deletion produced in the wA gene. The three strains showing bands having the same size were subjected to sequence analysis (using wAseqF and wAseqR, described in Table 5, as sequencing primers). As a result, all of these strains showed a one-base deletion.

TABLE 7

| Primer name | Sequence (5'→3') | SEQ ID NO: | Use |
|---|---|---|---|
| wAleftA-F | GATGGCCCTCTATTTTGTGC AAAGACTGACATGAC | 15 | Template amplification |
| wArightD-R | GGTAGGAAGCCTTGACAGCC AGCATGGCGTGT | 16 | Template amplification |

The invention claimed is:

1. A method of editing a gene in a koji fungal genome, the method comprising the step of:
   directly introducing a genome editing protein complex for a target gene into a cell of a koji fungus,
   wherein the genome editing protein complex is a complex containing a Cas9 protein and a guide RNA; complexes containing a nickase-modified Cas9 protein and each of a pair of guide RNAs; or a complex containing a nickase-modified or null mutant Cas9 protein to which a deaminase is linked and a guide RNA, and
   wherein the genome editing protein complex containing not less than 10 µg of said Cas9 protein is added with respect to $10^6$ koji fungal protoplasts in the direct introduction step.

2. The method according to claim 1, wherein the Cas9 protein is a Cas9 protein derived from *Streptococcus pyogenes*.

3. The method according to claim 2, wherein the guide RNA is a single-stranded RNA whose target sequence is a sequence adjacent to and upstream of an NGG sequence present in the target gene region, the single-stranded RNA comprising (1) a chimeric sequence comprising crRNA and tracrRNA and (2) a sequence identical to the target sequence except that U is placed instead of T, wherein the chimeric sequence (1) is linked to the 3'-side of the sequence (2).

4. The method according to claim 1, wherein the koji fungus is *Aspergillus oryzae*.

5. The method according to claim 1, wherein the editing of the target gene is disruption of the target gene.

6. The method according to claim 5, wherein the target gene is a drug sensitivity gene or a metabolic analog substance sensitivity gene.

7. A method of producing a koji fungal strain in which a gene in a genome is edited, the method comprising the steps of:
   directly introducing a genome editing protein complex for a target gene into cells of a koji fungus; and
   selecting and collecting a koji fungal cell in which the target gene is edited,
   wherein the genome editing protein complex is a complex containing a Cas9 protein and a guide RNA; complexes containing a nickase-modified Cas9 protein and each of a pair of guide RNAs; or a complex containing a nickase-modified or null mutant Cas9 protein to which a deaminase is linked and a guide RNA, and
   wherein the genome editing protein complex containing not less than 10 µg of said Cas9 protein is added with respect to $10^6$ koji fungal protoplasts in the direct introduction step.

8. A method of editing a plurality of genes in a koji fungal genome, the method comprising the step of:
   simultaneously directly introducing a first genome editing protein complex for a first target gene, and a second genome editing protein complex for a second target gene, into a koji fungal cell which has an ability of repair by non-homologous end-joining,
   wherein the first and second genome editing protein complexes each being selected from: a complex containing a Cas9 protein and a guide RNA; complexes containing a nickase-modified Cas9 protein and each of a pair of guide RNAs; and a complex containing a nickase-modified or null mutant Cas9 protein to which a deaminase is linked and a guide RNA, and wherein the genome editing complexes each containing not less than 10 µg of said Cas9 protein are added with respect to $10^6$ koji fungal protoplasts in the direct introduction step.

9. The method according to claim 8, wherein the Cas9 protein is a Cas9 protein derived from *Streptococcus pyogenes*.

10. The method according to claim 9, wherein the guide RNA is a single-stranded RNA whose target sequence is a sequence adjacent to and upstream of an NGG sequence present in the target gene region, the single-stranded RNA comprising (1) a chimeric sequence comprising crRNA and tracrRNA and (2) a sequence identical to the target sequence except that U is placed instead of T, wherein the chimeric sequence (1) is linked to the 3'-side of the sequence (2).

11. The method according to claim 8, wherein the koji fungus is *Aspergillus oryzae*.

12. The method according to claim 8, wherein at least one of the first and second target genes is a drug sensitivity gene or a metabolic analog substance sensitivity gene.

13. A method of producing a koji fungal strain having a plurality of edited genes in a genome, the method comprising the steps of:

simultaneously directly introducing a first genome editing protein complex for a first target gene, and a second genome editing protein complex for a second target gene, into koji fungal cells which have an ability of repair by non-homologous end-joining; and selecting and collecting a koji_fungal cell in which the first and second target genes are edited, wherein the first and second genome editing protein complexes each being selected from: a complex containing a Cas9 protein and a guide RNA; complexes containing a nickase-modified Cas9 protein and each of a pair of guide RNAs; and a complex containing a nickase-modified or null mutant Cas9 protein to which a deaminase is linked and a guide RNA, and wherein the genome editing complexes each containing not less than 10 µg of said Cas9 protein are added with respect to $10^6$ koji fungal protoplasts in the direct introduction step.

* * * * *